(12) United States Patent
Mezei

(10) Patent No.: US 10,087,197 B2
(45) Date of Patent: Oct. 2, 2018

(54) SELECTIVE EXTRACTION OF ANIONS FROM SOLUTION

(71) Applicant: Western Michigan University Research Foundation, Kalamazoo, MI (US)

(72) Inventor: Gellert Mezei, Kalamazoo, MI (US)

(73) Assignee: Western Michigan University Research Foundation, Kalamazoo, MI (US)

( * ) Notice: Subject to any disclaimer, the term of this patent is extended or adjusted under 35 U.S.C. 154(b) by 660 days.

(21) Appl. No.: 14/624,437

(22) Filed: Feb. 17, 2015

(65) Prior Publication Data

US 2015/0158749 A1     Jun. 11, 2015

Related U.S. Application Data

(63) Continuation-in-part of application No. 14/402,833, filed as application No. PCT/US2013/042035 on May 21, 2013, now Pat. No. 9,901,901.

(Continued)

(51) Int. Cl.
*C07F 1/08* (2006.01)
*B01D 17/02* (2006.01)
(Continued)

(52) U.S. Cl.
CPC .............. *C07F 1/08* (2013.01); *C02F 1/683* (2013.01); *C02F 2101/101* (2013.01);
(Continued)

(58) Field of Classification Search
None
See application file for complete search history.

(56) References Cited

U.S. PATENT DOCUMENTS 4,861,564 A    8/1989 Rebek
5,766,478 A    6/1998 Smith et al.
(Continued)

OTHER PUBLICATIONS

Govor et al., Chem. Commun., 2011, 47, 1764-1766.*
(Continued)

*Primary Examiner* — Allison G Fitzsimmons
(74) *Attorney, Agent, or Firm* — Price Heneveld LLP

(57) ABSTRACT

A method of selectively extracting anions from an aqueous solution using an anion encapsulating aggregate formed upon the addition of a solvent, a copper contributor, a hydroxide contributor, an optional counterion contributor, and at least one encapsulating anion to an aqueous solution containing the anions, or upon the addition of a solvent, a polymeric chain of $[Cu^{II}(\mu\text{-OH})(\mu\text{-ea})]_\infty$ and optionally, a counterion contributor to the aqueous solution. The aggregates include compounds of the formula cis-$Cu^{II}_x(OR_1)_y(R_2ea)_z$, where $R_1$ is H or an alkyl group, $R_2$ is H, or an alkyl group or a charged group, ea is an encapsulating anion, and each of x, y, and z is equal to an integer between about 1 and 40, inclusive. In addition, anion encapsulating aggregates can be formed by synthesis with alternate encapsulating anions by substituting alternate encapsulating anions for the encapsulating anion incorporated in the aggregate.

8 Claims, 8 Drawing Sheets

Related U.S. Application Data

(60) Provisional application No. 61/649,491, filed on May 21, 2012.

(51) Int. Cl.
    *C02F 101/10*      (2006.01)
    *C02F 101/22*      (2006.01)
    *C02F 1/68*      (2006.01)

(52) U.S. Cl.
    CPC .. *C02F 2101/103* (2013.01); *C02F 2101/105* (2013.01); *C02F 2101/106* (2013.01); *C02F 2101/22* (2013.01); *C02F 2305/00* (2013.01)

(56) References Cited

U.S. PATENT DOCUMENTS

| | | |
|---|---|---|
| 2011/0033401 A1 | 2/2011 | Morrissey et al. |
| 2011/0309017 A1 | 12/2011 | Hassler et al. |
| 2012/0065614 A1 | 3/2012 | Omary et al. |

OTHER PUBLICATIONS

STIC Structure search results, 222 pages, Sep. 30, 2017.*

Mezei, Gellert et al., "Anion Encapslation by Neutral Supramolecular Assemblies of Cyclic CuII Complexes: A Series of Five Polymerization Isomers, [{cis-CuII($\mu$-OH)($\mu$-pz)}n], n=6, 8, 9, 12, and 14," Angew. Chem. Int. Ed. 2004, vol. 43, pp. 573-577.

Mezei, Gellert et al., "Effect of copper-substitution on the structure and nuclearity of Cu(II)-pyrazolates: from trinuclear to tetra-, hexa- and polynuclear complexes," Inorganica Chimica Acta, Apr. 2004, vol. 357, pp. 3721-3732.

Mohamed, Ahmed A. et al., Self-assembly of a High-Nuclearity Chloride-Centered Copper(II) Cluster. Structure and Magnetic Properties of [Au(PPh3)2][trans-Cu6($\mu$-OH)6{3,5-CF3)2pz}6Cl], Inorganic Chemistry, Mar. 2007, vol. 46, No. 7, pp. 2348-2349.

Pettinari, Claudio et al., "Tuning the Functional Properties of Metal Complexes Containing Polytopic Heteroaromatic Nitrogen Ligands," Chem. Eur. J., 2010, vol. 16, pp. 1106-1123.

Moyer, Bruce A. et al., "Enhanced liquid-liquid anion exchange using macrocyclic anion receptors: effect of receptor structure on sulphate-nitrate exchange selectivity," Supramolecular Chemistry, Nov.-Dec. 2010, vol. 22, Nos. 11-12, pp. 653-671.

Rajbanshi, Arbin et al., "Sulfate Separation from Aqueous Aklaline Solutions by Selective Crystallization of Alkali Metal Coordination Capsules," American Chemical Society, 2011, vol. 11, pp. 2702-2706.

Fernando, Isurika R. et al., "Selective total encapsulation of the sulfate anion by neutral nano-jars," Chem. Commun., 2012, vol. 48, pp. 6860-6862.

European Patent Office, Examination Report for European Application No. 13804080.3, dated Oct. 25, 2017, 11 pages.

G.A. Ardizzoia et al., Reaction of Dioxygen with [Cu(dmpz)]n (Hdmpz=3,5-Dimethylpyrazole). Crystal Structure, Reactivity, and Catalytic properties of [Cu8(dmpz)8(OH)8], Inorg. Chem. E. I. J. Am. Chem. SOC, Jan. 1, 191, pp. 4347-4353.

Mezei, Gellert et al.; "Anion Encapsulation by Neutral Supramolecular Assemblies of Cyclic CuII-Complexes; a Series of Five Polymerization Isomers"; Supporting Information; Angewandte Chemie; 2003; 3 pages; Weinheim, Germany.

Angaridis, Panagiotis et al.; "Synthesis and Structural Characterization of Trinuclear CuII-Pyrazolato Complexes Containing . . . "; Article; Inorganic Chemistry; Mar. 25, 2002; vol. 41, No. 8; pp. 2219 to 2228; American Chemical Society.

\* cited by examiner

SELECTIVE EXTRACTION OF ANIONS FROM SOLUTION

CROSS-REFERENCE TO RELATED APPLICATIONS

This application is a continuation-in-part that claims priority to and benefit under 35 U.S.C. § 120 of U.S. patent application No. 14/402,833, filed Nov. 21, 2014, entitled SELECTIVE EXTRACTION OF ANIONS FROM SOLUTION," now U.S. Pat. No. 9,901,901, which claims priority to and the benefit under 35 U.S.C. § 119(e) of International Patent Application No. PCT/US2013/042035, filed Nov. 21, 2014, entitled "SELECTIVE EXTRACTION OF ANIONS FROM SOLUTION," which are each hereby incorporated herein by reference in thier entirety.

FIELD OF THE INVENTION

The invention is in the field of the selective extraction of anions from solution.

BACKGROUND

Selective extraction of specific anions from a solution can be useful in several different contexts, but has been limited in practice by the inability of anion extraction to overcome the Hofmeister bias. In liquid-liquid anion extraction, the Hofmeister bias is a thermodynamic bias that favors the extraction of charge diffuse, weakly hydrated anions from water into an organic medium. Therefore, if the anion which is desired to be extracted is in competition with an anion which is more charge diffuse and weakly hydrated, selective extraction of the desired anion must overcome the Hofmeister bias.

One example of a system where two anions are in aqueous solution, and it is desirable to remove one of the anions selectively from the solution, is nuclear waste, where both nitrates and sulfates are in solution. Sulfate separation is desirable to improve vitrification of the nuclear waste, but the Hofmeister bias greatly favors the extraction of nitrate from the solution instead of sulfate.

Sulfate separation is also desirable for waste streams to avoid affecting natural biogeochemical cycles and the metabolisms of living organisms. The uncontrolled release of anthropogenic sulfate can have a significant impact on the environment, such as by increasing Earth's albedo or leading to eutrophication of rivers or lakes.

Extraction of other anions from a liquid solution in contravention to the usual Hofmeister bias is also desirable in certain liquid handling and separations situations. Additional anions for preferential extraction may include phosphate, arsenate, chloride, carbonate, fluoride, selenate, selenite, sulfite, chromate, pyrophosphate, arsenite, and tetrafluoroberyllate.

Phosphate, along with sulfate, leads to eutrophication of lakes and rivers, therefore methods for the specific removal of phosphates, in addition to sulfates, from water entering lakes and rivers are highly sought after, such as removal of phosphates and sulfates widely used in fertilizer from agricultural runoff. Chloride has also been found to accumulate in lakes due to the use of large amounts of road-salt (NaCl, $CaCl_2$) in the winter, and cause adverse environmental effects. Therefore, preferential removal of chloride from such environments is desirable. Anions such as chromate, arsenate, arsenite, selenate, selenite, and tetrafluoroberyllate are highly toxic, therefore they need to be removed very efficiently from waste waters at industrial and mining sites, or water purification plants.

BRIEF SUMMARY

In one aspect, the present innovation includes an anion-encapsulating compound, including an encapsulating host of the formula cis-$Cu^{II}_x(OR_1)_y(R_2ea)_z$. $R_1$ is H, $CH_3$, $C_2H_5$, $C_3H_7$, $C_4H_9$ or another alkyl group, $R_2$ is H, $CH_3$, $C_2H_5$, $C_3H_7$, $C_4H_9$ or another alkyl or charged group, and ea is a first encapsulating anion having a core with two donor atoms on one side at 1.3 angstroms to 2.5 angstroms apart, with no other atoms substantially hindering the coordination of the donor atoms to the copper metal centers. Each of x, y, and z is equal to an integer between about 1 and 40, inclusive.

In another aspect, the present innovation includes a method of selectively extracting a targeted anion from an aqueous solution. The method includes the steps of combining a solvent and anion-encapsulating components with the aqueous solution containing the targeted anion to form an organic-aqueous mixture that has an overall neutral or basic pH level. The organic-aqueous mixture has an organic phase and an aqueous phase. The anion-encapsulating components include a copper ion contributor, a hydroxide ion contributor, and at least one encapsulating anion contributor. The anion-encapsulating components are allowed to react to form encapsulating hosts in situ in the organic-aqueous mixture around the target anions to contain the target ions therein. The target anion is chosen from the group consisting of sulfate, phosphate, arsenate, carbonate, selenate, selenite, sulfite, chromate, tetrafluoroberyllate, pyrophosphate and arsenite. The organic phase and the aqueous phase are separated.

In another aspect, the present innovation includes a method of selectively extracting a targeted anion from an aqueous solution. The method includes the steps of combining a solvent, a polymer chain of $[Cu^{II}(\mu\text{-OH})(\mu\text{-ea})]_\infty$, where ea is an encapsulating anion, and an aqueous solution containing the target anion to form an organic-aqueous mixture that has an overall neutral or basic pH level. The organic-aqueous mixture has an organic phase and an aqueous phase. The polymer chain is allowed to form an encapsulating host around the target anion. The target anion is chosen from the group consisting of sulfate, phosphate, arsenate, carbonate, selenate, selenite, sulfite, chromate, tetrafluoroberyllate, pyrophosphate and arsenite ions. The organic phase is separated from the aqueous phase.

These and other features, advantages, and objects of the present invention will be further understood and appreciated by those skilled in the art by reference to the following specification, claims, and appended drawings.

DETAILED DESCRIPTION

Figure 1:
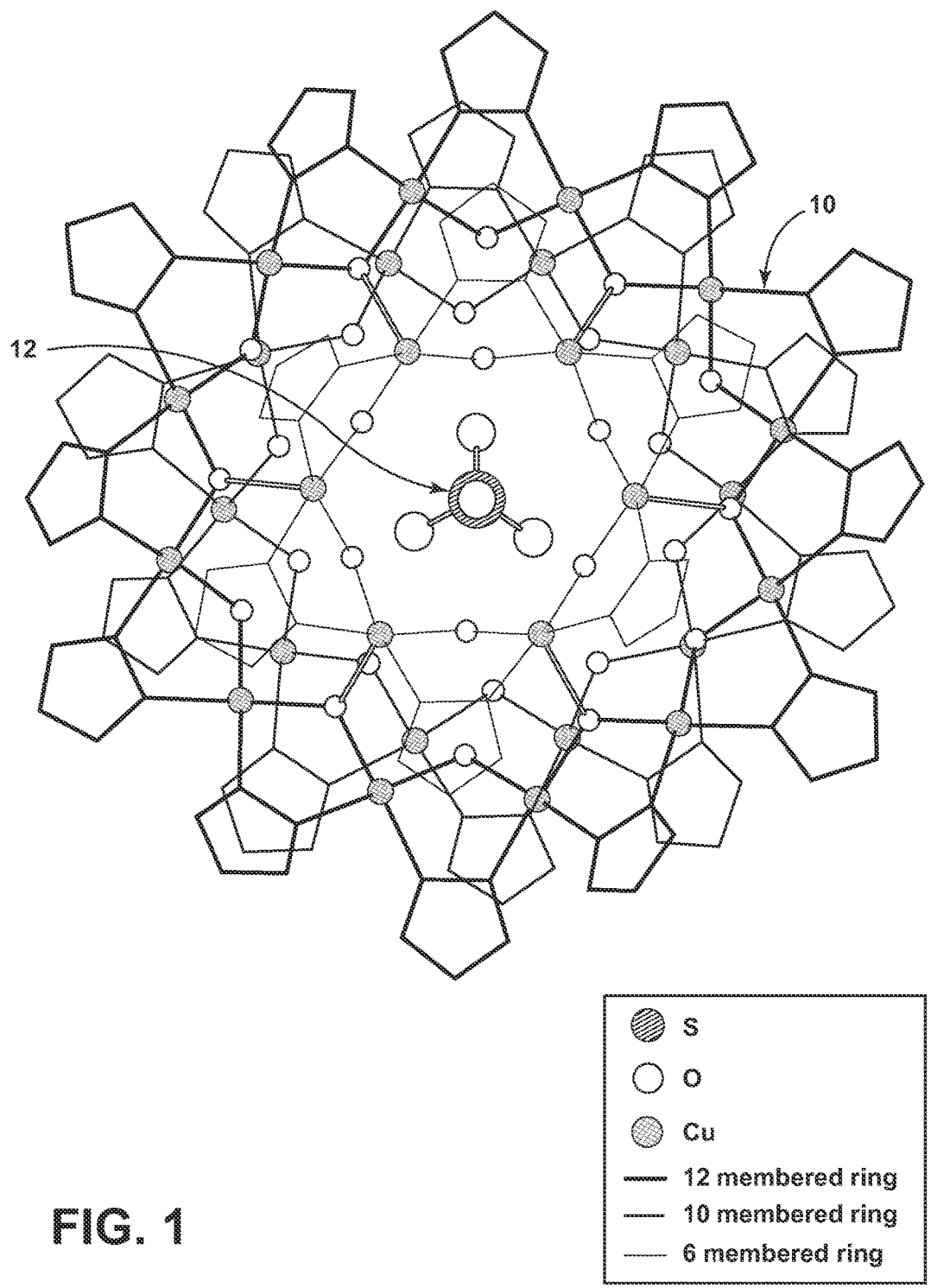
FIG. 1 is a top view of sulfate encapsulated in an encapsulating host, represented by the formula $SO_4^{2-} \subset \{cis\text{-}Cu^{II}(\mu\text{-OH})(\mu\text{-pz})\}_{6+12+10}(SO_4^{2-} \subset \{cis\text{-}Cu^{II}(\mu\text{-OH})(\mu\text{-pz})\}_{28})$.

Various example embodiments are described herein. However, it is to be understood that the invention may assume various alternative embodiments or orientations except where expressly specified to the contrary. It is also to be understood that the specific embodiments and processes illustrated in the attached drawings and described in the following specification are simply exemplary and that those skilled in the art will be able to substitute various alternative components or counterions, or use alternative solvents, pH-adjusting compounds or other components without affecting the functional structure of the anion-encapsulating aggregates described herein or the method of removal of the anions from solution. Hence, specific methods of synthesis, dimensions and other physical characteristics relating to the embodiments disclosed herein are not to be considered as limiting. Throughout the disclosure, relevant terms are to be understood consistently with their typical meanings in the relevant art, unless otherwise defined herein.

Certain embodiments of anion-encapsulating aggregates based on a series of compounds are described herein, as well as methods of using the anion-encapsulating aggregates to remove targeted anions from solution. In one embodiment, the anion-encapsulating aggregate is based on an encapsulating host, where the host has the formula cis-$Cu^{II}_x(OR_1)_y(R_2ea)_z$, where $R_1$ is H, $CH_3$, $C_2H_5$, $C_3H_7$, $C_4H_9$ or another alkyl group, $R_2$ is H, $CH_3$, $C_2H_5$, $C_3H_7$, $C_4H_9$ or another alkyl or charged group, ea is an encapsulating anion, and each of x, y, and z is equal to an integer between about 1 and 40, inclusive. In one preferred embodiment, the encapsulating anion is pyrazolate (pz). In various alternative embodiments the pyrazolate anion can be replaced at least in part by an alternate, encapsulating anion, such as ligand-bound pyrazolate anions (where the pyrazolate is bound to either charged ligands or an alkyl group), indazolate anions; methylpyrazolate anions; dimethylpyrazolate anions; ethylene-bridged pyrazolate anions (2 pyrazole linked by 2 $CH_2$ groups); propylene-bridged pyrazolate anions (2 pyrazole linked by 3 $CH_2$ groups); butylene-bridged pyrazolate anions (2 pyrazole linked by 4 $CH_2$ groups); pentylene-bridged pyrazolate anions (2 pyrazole linked by 5 $CH_2$ groups); hexylene-bridged pyrazolate anions (2 pyrazole linked by 6 $CH_2$ groups); heptylene-bridged pyrazolate anions (2 pyrazole linked by 7 $CH_2$ groups); octylene-bridged pyrazolate anions (2 pyrazole linked by 8 $CH_2$ groups); carboxylate anions, including without limitation formate anions and acetate anions; or another encapsulating ligand having a core with two donor atoms (N, O, etc.) on one side at about 1.3-2.5 angstroms apart (with no other atoms substantially hindering the coordination of these two donor atoms to the copper centers). Some additional non-limiting examples of such ligands include 7-azaindole, 1,4,6-triazabicyclo[3.3.0]oct-4-ene, 1,3,4,6,7,8-hexahydro-2H-pyrimido[1,2-a]pyrimidine and 1,4,6-triazabicyclo[3.4.0]non-4-ene. As used herein, unless the context specifically indicates otherwise, where "pz" or pyrazolate is used, it is understood that the pyrazolate anion can be replaced at least in part by the various alternate anions and ligands discussed above, and can be replaced completely by ligand-bound pyrazolate anions (where the pyrazolate is bound to either charged ligands or an alkyl group), indazolate anions, or ethylene-bridged pyrazolate anions. Where the nanojars are formed using pyrazolate anions or a replacement for pyrazolate anions which is capable of completely replacing the pyrazolate, the core of the resulting ligand is not wider than about 6 angstroms.

One preferred set of embodiments includes anion-encapsulating aggregates based on a series of compounds of the formula cis-$Cu^{II}_x(OR)_y(ea)_z$, where R is H, $CH_3$, or another alkyl group, ea is a pyrazolate anion and each of x, y, and z is equal to an integer between about 1 and about 40, inclusive. Another particular embodiment of this compound is a cyclic polymerization isomer of the formula [cis-$Cu^{II}$($\mu$-OH)($\mu$-pz)]$_n$, where n is an integer between about 6 and about 16, inclusive. As used herein, u means "bridging," meaning that where "$\mu$-OH" is used, the O atom of the OH group bridges two adjacent copper centers. Similarly, where "$\mu$-pz" is used, the two N atoms of the pyrazolate ligand are bound to two different copper atoms, and therefore the pyrazolate ligand is bridging two adjacent copper centers. Where "$\mu_3$-OH" is used below, it means that the O atom of the OH group bridges three adjacent copper centers.

In another preferred set of embodiments, the pyrazolate (pz) of the formula cis-$Cu^{II}_x(OR)_y(pz)_z$ is replaced at least in part by an alternate encapsulating anion, as described herein. In certain preferred embodiments, the pyrazole is completely replaced by ligand-bound pyrazolate anions (where the pyrazolate is bound to either charged ligands or an alkyl group); indazolate anions; methylpyrazolate anions; ethylene-bridged pyrazolate anions (2 pyrazole linked by 2 $CH_2$ groups); or another encapsulating ligand having a core with two donor atoms (N, O, etc.) on one side at about 1.3-2.5 angstroms apart (with no other atoms substantially hindering the coordination of these two donor atoms to the copper centers), and with the core of the ligand being less than about 6 angstroms across. To produce these variations, the anion-encapsulating aggregates can first be formed with pyrazolate anions, and then at least a portion of the pyrazolate anions replaced, or can be formed with a combination of pyrazolate anions and alternate encapsulating anions.

In certain embodiments, if there is steric hindrance to the coordination of the donor atoms to the copper centers, inclusion of a second encapsulating anion without substantial steric hindrance in this position may allow a ligand having some steric hindrance to be incorporated as an encapsulating anion in combination with the other ligand which does not have steric hindrance. In another set of preferred embodiments, the pyrazole is only partially replaced by indazolate anions; methylpyrazolate anions; dimethylpyrazolate anions; ethylene-bridged pyrazolate anions (2 pyrazole linked by 2 $CH_2$ groups); propylene-bridged pyrazolate anions (2 pyrazole linked by 3 $CH_2$ groups); butylene-bridged pyrazolate anions (2 pyrazole linked by 4 $CH_2$ groups); pentylene-bridged pyrazolate anions (2 pyrazole linked by 5 $CH_2$ groups); hexylene-bridged pyrazolate anions (2 pyrazole linked by 6 $CH_2$ groups); heptylene-bridged pyrazolate anions (2 pyrazole linked by 7 $CH_2$ groups); octylene-bridged pyrazolate anions (2 pyrazole linked by 8 $CH_2$ groups); carboxylate anions, including without limitation formate anions and acetate anions; or another encapsulating ligand having a core with two donor atoms (N, O, etc.) on one side at about 1.3-2.5 angstroms apart (with no other atoms substantially hindering the coordination of these two donor atoms to the copper centers). To produce these variations, the anion-encapsulating aggregates can first be formed with pyrazolate anions, and then at least a portion of the pyrazolate anions replaced, or can be formed with a combination of pyrazolate anions and alternate encapsulating anions.

Such anion-encapsulating aggregates can be used to selectively extract target anions of sulfate, phosphate, arsenate, carbonate, and chromate anions preferentially from a solution, and are also believed to be useful in separating selenate, selenite, sulfite, tetrafluoroberyllate, pyrophosphate, and arsenite anions preferentially from a solution.

The anion host assemblies described herein, form "nano-jars" or toroids of the host around the anion to be extracted in solution, as further described below. The anion host assemblies exhibit a large number of hydrogen-bonds between the targeted anion and the rings and strands of the host assemblies, resulting in encapsulation of the targeted anion by the host assemblies, and sequestration of the targeted anion, an example of which is shown in FIGS. 1-2.

Figure 2:
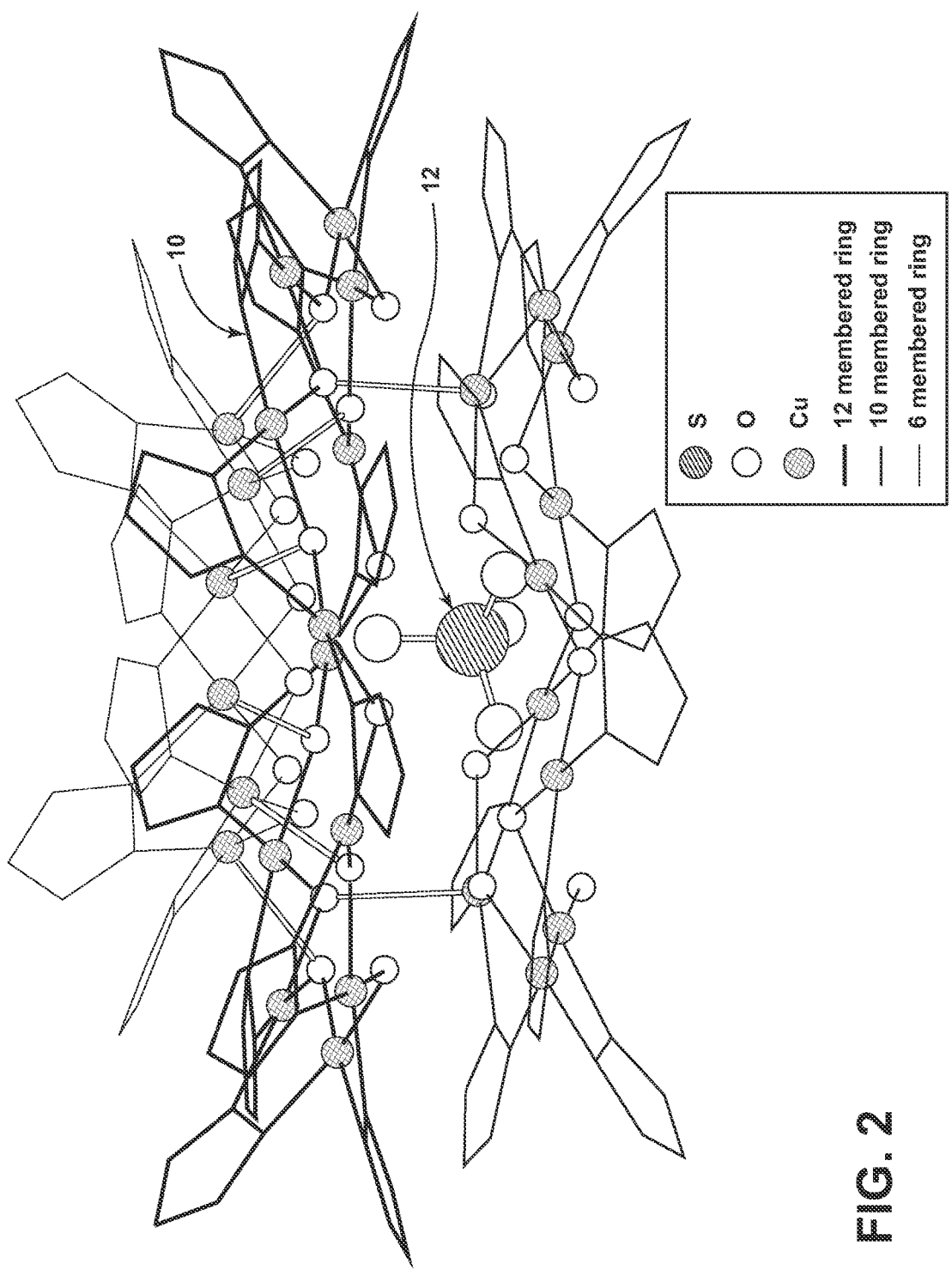
FIG. 2 is a side plan view of the sulfate encapsulated in an encapsulating host, represented by the formula $SO_4^{2-} \subset \{cis\text{-}Cu^{II}(\mu\text{-OH})(\mu\text{-pz})\}_{28}$, as shown in FIG. 1.

FIG. 1 is a top view of $SO_4^{2-} \subset \{cis\text{-}Cu^{II}(\mu\text{-}OH)(\mu\text{-}pz)\}_{6+12+10}$, where 6-member pyrazole ligand rings, 12-member pyrazole ligand rings, and 10-member pyrazole ligand rings form a 29-member pyrazole ligand "nano-jar" 10 around the target anion 12. FIG. 2 is a side plan view of the encapsulating host which forms the nano-jar 10 and the target anion 12.

Figure 3:
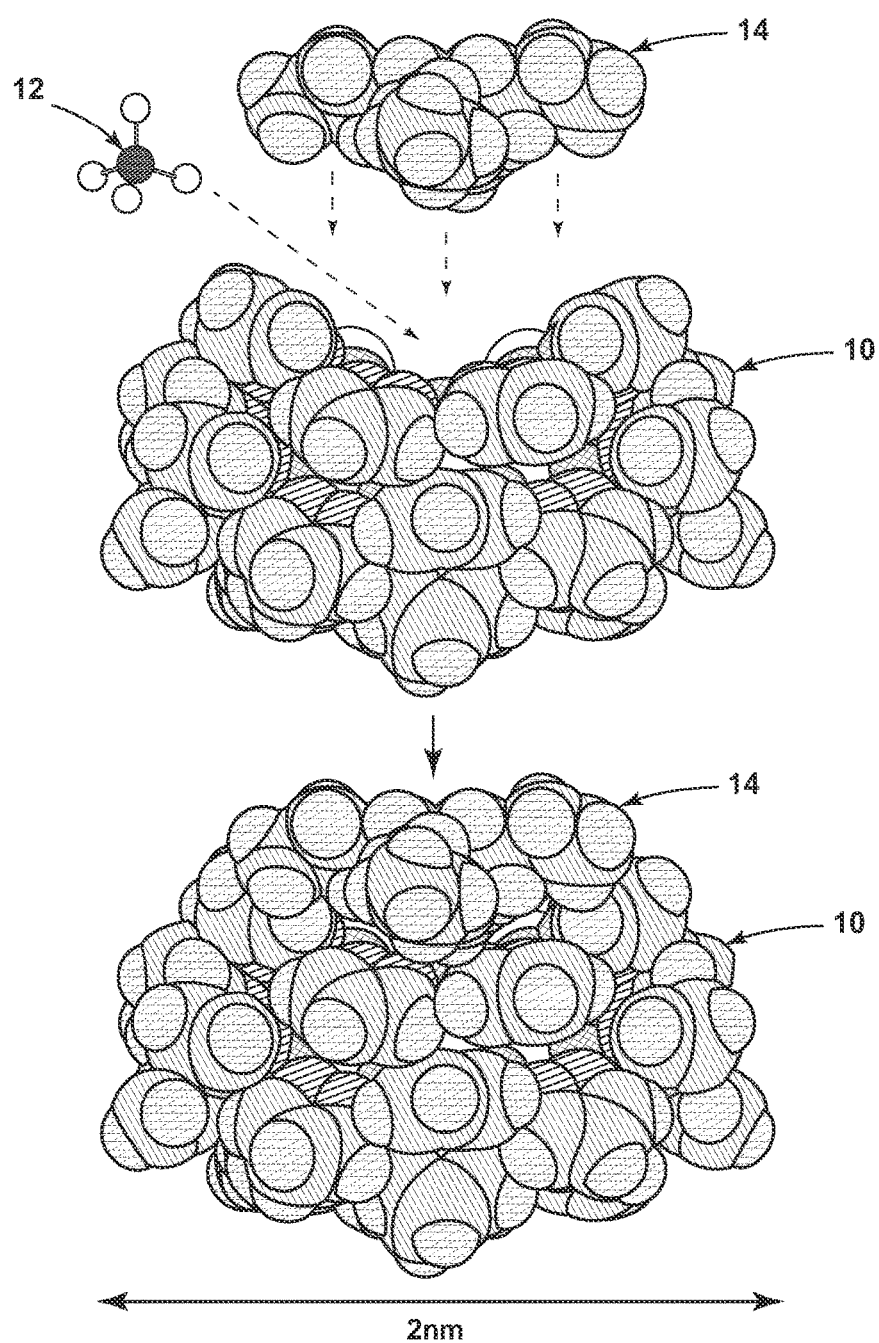
FIG. 3 is a side plan view showing the formation of the sulfate-encapsulating nano-jar.
Figure 4:
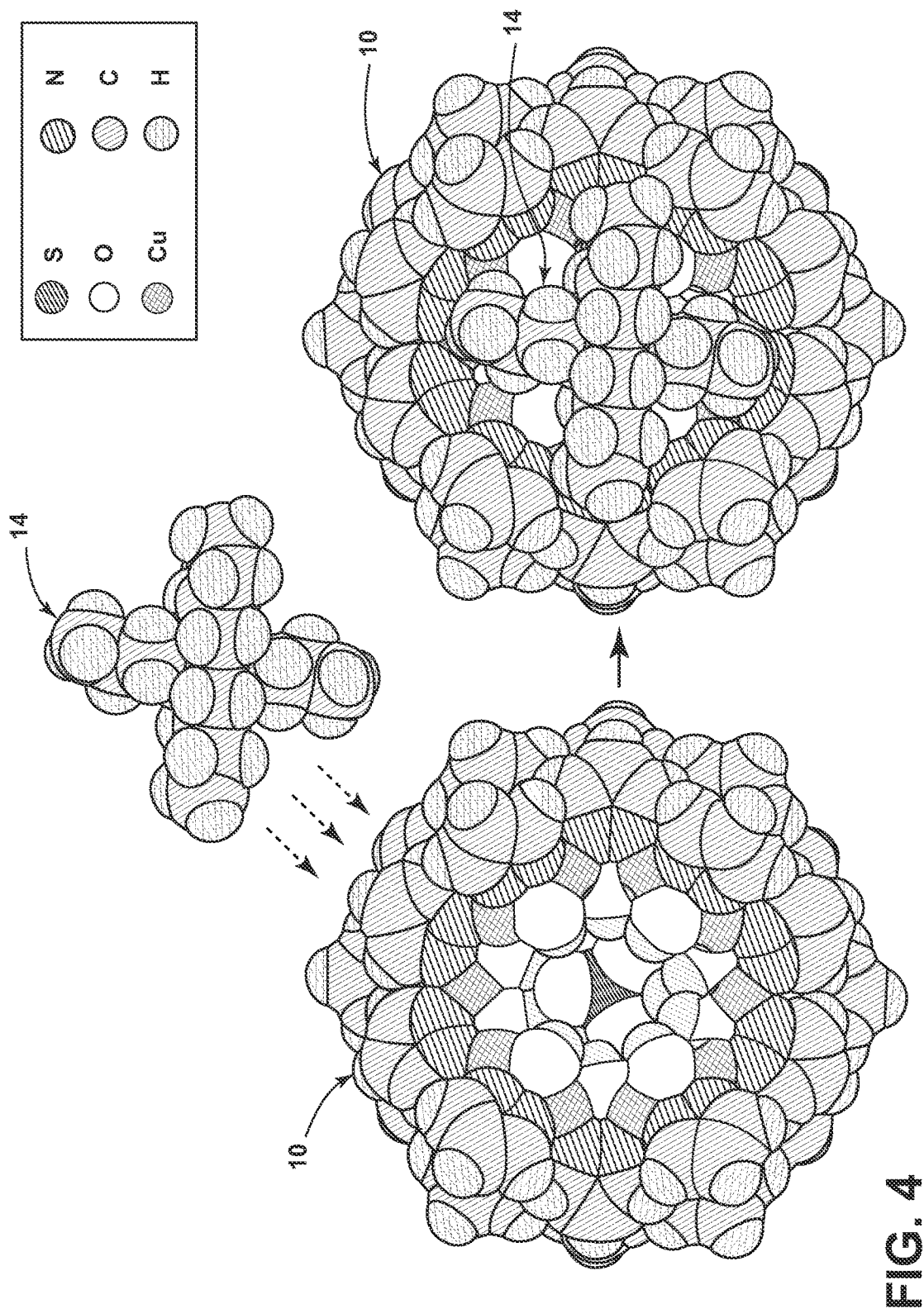
FIG. 4 is a top view showing the formation of the sulfate-encapsulating "nano-jar;"

As shown in FIGS. 3-4, a suitable counterion, when added to the solution of nano-jar 10 forming host assemblies in certain solvent environments, further associates with the host assembly to form a lid 14 for the nano-jar 10 to complete the anion-encapsulating aggregate. One set of suitable counterions include large cations. Potential large counterions include, but are not limited to counterions such as tetrabutylammonium ($Bu_4N^+$), tributylammonium ($Bu_3NH^+$), tetraethylammonium ($Et_4N^+$), triethylammonium ($Et_3NH^+$), 18-crown-6 potassium complex ($K^+$-18C6), tris(1,10-phenanthroline)copper(II)-[$Cu(phen)_3$]$^{2+}$, and bis(triphenylphosphoranylidene)ammonium ($Ph_3P=N=PPh_3^+$). Additional cation counterions can be used to form the lid for the nano-jar, including smaller alkali or alkaline-earth metal cation counterions. Non-limiting examples of such smaller counterions include sodium, potassium, rubidium, cesium, and barium ions.

However, the attachment of the lid 14 to the nano-jar 10 is not required for selective anion extraction. The nano-jars 10 described herein self-assemble around the particular targeted anion 12 during the extraction process. The lid 14 will generally be attached to the nano-jar 10 if the solvent is fairly non-polar (such as chloroform), but will generally be detached if the solvent is polar (such as dimethylsulfoxide). The binding strength of the nano-jars 10 toward target anions 12 is independent of the lid 14. Addition of the lid 14 creates a compound which is soluble in certain solutions.

To perform a liquid-liquid extraction to extract a target anion from an aqueous solution using the anion host assemblies as described herein, one preferred method is to combine a solvent and the nano-jar components, including a copper salt, an encapsulating anion, and a base, with an aqueous solution containing the anion(s) to be extracted to form an organic-aqueous mixture that has an overall neutral or basic pH level (a pH level in the range of 7 to 14). The solvent and nano-jar components can be added together (with the components dissolved or suspended in the solvent, or with one or more of the components combined with the solvent or each other), or can be added individually in any order to the aqueous solution to form the organic-aqueous mixture, having an organic phase and an aqueous phase. The components in the organic-aqueous mixture are then permitted to react while the organic-aqueous mixture has a neutral or basic pH level. During such reaction, the encapsulating host assemblies begin forming in situ in the organic-aqueous mixture, around the target anions, even if other competing anions which would normally be favored by the Hofmeister bias are present in the aqueous phase. As the nano-jars form, they transfer to the organic phase. The organic phase and aqueous phase can then be separated using known separation techniques therefor, such as a separatory funnel. Upon separation, the target anions and encapsulating host assemblies are removed in the organic phase, leaving an aqueous phase from which some or all of the target anions have been removed.

A compound containing or capable of providing a suitable counterion upon reaction, a counterion contributor, is also optionally added to the organic-aqueous mixture to act as the lid for the nano-jars and to complete an anion-encapsulating aggregate. If bases such as triethylamine or tributylamine are used, there is no need to add a separate counterion contributor because the triethylammonium or tributylammonium ions resulting from the self-assembly reaction (by protonation of the base) will serve as suitable counterion lids. Suitable counterions include, without limitation, sodium ions ($Na^+$), potassium ions ($K^+$), rubidium ions ($Rb^+$), calcium ions ($Ca^+$), cesium ions ($Cs^+$), thallium ions ($Tl^+$), strontium ions ($Sr^{2+}$), barium ions ($Ba^{2+}$), tetrabutylammonium ions ($Bu_4N^+$), tributylammonium ($Bu3NH+$), tetraethylammonium ($Et4N+$), triethylammonium ($Et3NH+$), 18-crown-6 potassium complex ($K^+$-18C6), tris(1,10-phenanthroline)copper(II)-[$Cu(phen)_3$]$^{2+}$, and bis(triphenylphosphoranylidene)ammonium ($Ph_3P=N=PPh_3^+$). The solvents used in addition to the nano-jar components are believed to have little or no influence on the self-assembly process of the "nano-jars." If the extraction is performed without a suitable counterion, the reaction may lead to an insoluble material, hampering removal of the target anion from the aqueous phase of the liquid. Illustration of the addition of the lid to an encapsulated target anion is shown in FIG. 4.

Suitable copper salts may include copper nitrate, copper perchlorate, copper tetrafluoroborate, or other copper salts having copper combined with another anion having a small hydration energy, which contribute a copper ion for formation of the anion-encapsulating assembly. Suitable bases include, but are not limited to, bases such as potassium hydroxide, sodium hydroxide, triethylamine, tributylamine, tetrabutylammonium hydroxide, and trialkylamines, all of which contribute or cause the contribution of a hydroxide ion for the formation of the anion-encapsulating assembly.

Alternatively, instead of adding a copper salt and a base, $Cu(OH)_2$ can be added to the solution to replace the copper salt and the base listed above. The $Cu(OH)_2$ behaves as a copper-ion contributor (as the copper salt does), and also as a hydroxide ion contributor (as the base does). Suitable solvents may include toluene, tetrahydrofuran, chloroform, dichloromethane or other solvents. To facilitate separation of the organic and aqueous phases of the liquid, the solvent used cannot be miscible with water under the final conditions of the reaction (when the anion-encapsulating hosts and target anions are present in the organic phase). For example, despite the fact that tetrahydrofuran (THF) is normally miscible with water, the THF will form a phase separate from the aqueous phase solution at high ionic strengths.

Another method of preparing an encapsulating assembly includes the steps of providing a first encapsulating host, the first encapsulating host including a copper ion contributor, a hydroxide ion contributor and at least one encapsulating anion. The anion-encapsulating components are allowed to react to form encapsulating hosts in situ in the organic-aqueous mixture around the target anions. In certain embodiments, the at least one encapsulating anion is chosen from the group comprising pyrazolate anions, indazolate anions, ligand-bound pyrazolate anions (where the pyrazolate is bound to either charged ligands or an alkyl group), or ethylene-bridged pyrazolate anions. In other embodiments, the at least one encapsulating anion includes a pyrazolate anion and at least one of indazolate anions; ligand-bound pyrazolate anions (where the pyrazolate is bound to either charged ligands or an alkyl group), methylpyrazolate anions; dimethylpyrazolate anions; ethylene-bridged pyrazolate anions; propylene-bridged pyrazolate anions; butylene-bridged pyrazolate anions; pentylene-bridged pyrazolate anions; hexylene-bridged pyrazolate anions; heptylene-bridged pyrazolate anions; octylene-bridged pyrazolate anions; carboxylate anions, including without limitation formate anions and acetate anions; or another encapsulating ligand having a core with two donor atoms (N, O, etc.) on one side at about 1.3-2.5 angstroms apart (with no other atoms substantially hindering the coordination of these two donor atoms to the metal centers).

Another method of preparing an encapsulating assembly includes the steps of providing an encapsulating host, the encapsulating host including a copper ion contributor, a hydroxide ion contributor and a pyrazole. An alternate encapsulating anion is substituted for at least some of the pyrazole in the encapsulating host to form a modified encapsulating host. The encapsulating anion is chosen from the group consisting of indazolate anions; ligand-bound pyrazolate anions (where the pyrazolate is bound to either charged ligands or an alkyl group); methylpyrazolate anions; dimethylpyrazolate anions; ethylene-bridged pyrazolate anions; propylene-bridged pyrazolate anions; butylene-bridged pyrazolate anions; pentylene-bridged pyrazolate anions; hexylene-bridged pyrazolate anions; heptylene-bridged pyrazolate anions; octylene-bridged pyrazolate anions; carboxylate anions, including without limitation formate anions and acetate anions; or another encapsulating ligand having a core with two donor atoms (N, O, etc.) on one side at about 1.3-2.5 angstroms apart (with no other atoms substantially hindering the coordination of these two donor atoms to the metal centers). The anion-encapsulating components are allowed to react to form encapsulating hosts in situ in the organic-aqueous mixture around the target anions. The alternate encapsulating anion, if used, can be added before or after formation of the encapsulating hosts.

Another method for performing a liquid-liquid extraction of a target anion is to add a solvent, a polymer chain of $[Cu^{II}(\mu\text{-}OH)(\mu\text{-}pz)]_\infty$ and optionally, a suitable counterion contributor to an aqueous solution containing the targeted anion for extraction, to form an organic-aqueous mixture that has an overall neutral or basic pH level. The components in the organic-aqueous mixture are then permitted to react. Upon such reaction, the nano-jars self-assemble around the target anions and transfer into the organic phase, selectively removing the target anion from the aqueous phase. Separation of the organic phase from the aqueous phase results in extraction of some or all of the targeted anion from the aqueous phase. As described above, the pyrazole can be replaced at least in part by anions such as indazolate anions; ligand-bound pyrazolate anions (where the pyrazolate is bound to either charged ligands or an alkyl group); methylpyrazolate anions; dimethylpyrazolate anions; ethylene-bridged pyrazolate anions; propylene-bridged pyrazolate anions; butylene-bridged pyrazolate anions; pentylene-bridged pyrazolate anions; hexylene-bridged pyrazolate anions; heptylene-bridged pyrazolate anions; octylene-bridged pyrazolate anions; carboxylate anions, including without limitation formate anions and acetate anions; or another encapsulating ligand having a core with two donor atoms (N, O, etc.) on one side at about 1.3-2.5 angstroms apart (with no other atoms substantially hindering the coordination of these two donor atoms to the copper centers).

As described above, the solvent, polymer chain, and counterion contributor can be added together (with the components dissolved or suspended in the solvent, or with one or more of the components combined with the solvent or each other), or can be added individually in any order to the aqueous solution to form the organic-aqueous mixture that has an overall neutral or basic pH level. Suitable solvents and counterions for such reaction are the same as those described above.

Including certain metal ions during the formation of the nano-jars also influences formation of the anion-encapsulating aggregates and anion host assemblies, resulting in the formation of specific anion host assemblies. Metals which are preferred for influencing the formation of the nano-jars include without limitation lead, calcium, cobalt, manganese, praseodymium, neodynium, zinc, cadmium, and nickel. To use such metals to influence the formation of the anion host assemblies or anion-encapsulating aggregates, metal ions or compounds capable of contributing the metal ions are added to the solution while the anion-encapsulating aggregates are forming.

As used throughout the following description, unless stated otherwise in a particular instance, the formulas given for specific anion-encapsulating host assemblies and aggregates will be the formula of the solid compound that is present upon drying of the solvent.

One preferred embodiment of an anion-encapsulating aggregate is based on the three-ring $\{cis\text{-}Cu^{II}(\mu\text{-}OH)(\mu\text{-}pz)\}_{6+12+10}$ encapsulating host assembly ("Host 1"), as shown in FIG. 1 and FIG. 2. Host 1 can also be denoted as $\{cis\text{-}Cu^{II}(\mu\text{-}OH)(\mu\text{-}pz)\}_{28}$, and is one ring set that is representative of $\{cis\text{-}Cu^{II}(\mu\text{-}OH)(\mu\text{-}pz)\}_{28}$. The two opposite sides of the 6+12 membered ring assembly in this host assembly are curved upwardly, indicating the flexibility of the Cu-rings. Another preferred embodiment is based on the three-ring $\{cis\text{-}Cu^{II}(\mu\text{-}OH)(\mu\text{-}pz)\}_{8+14+9}$ encapsulating host assembly ("Host 2"). Similar to Host 1, Host 2 can also be denoted as $\{cis\text{-}Cu^{II}(\mu\text{-}OH)(\mu\text{-}pz)\}_{31}$, and is one ring set that is representative of $\{cis\text{-}Cu^{II}(\mu\text{-}OH)(\mu\text{-}pz)\}_{28}$.

Host 1 and Host 2 show selectivity for the encapsulation of sulfate ions over nitrate and perchlorate ions, and are believed to allow selective extraction of sulfate in the presence of chlorate, bromate, iodate, periodate, cyanate, trifluoromethansulfonate, permanganate, perrhenate, pertechnetate, picrate, tetrafluoroborate, tetraphenylborate, hexafluorophosphate and other anions that have a Gibbs free energy of hydration smaller than ~310 KJ/mol. Partial selectivity for the sulfate ion by Host 1 and Host 2 has also been observed in the presence of fluoride, chloride and bromide ions.

Host 1 and Host 2 each exhibit a large number of hydrogen-bonds between the sulfate anion and the two smaller rings in each assembly. This encapsulation of the sulfate by neutral hydrogen bond donors is on par with sulfate-binding proteins occurring in nature that sequester sulfate anions.

The encapsulating host assemblies in Host 1 and Host 2 include nano-jars of $\{cis\text{-}Cu^{II}(\mu\text{-}OH)(\mu\text{-}pz)\}_{6+12+10}$ and $\{cis\text{-}Cu^{II}(\mu\text{-}OH)(\mu\text{-}pz)\}_{8+14+9}$, respectively, which serve to encapsulate the sulfate ions, forming the compounds $SO_4^{2-} \subset \{cis\text{-}Cu^{II}(\mu\text{-}OH)(\mu\text{-}pz)\}_{6+12+10}$ or $SO_4^{2-} \subset \{cis\text{-}Cu^{II}(\mu\text{-}OH)(\mu\text{-}pz)\}_{28}$ and $SO_4^{2-} \subset \{cis\text{-}Cu^{II}(\mu\text{-}OH)(\mu\text{-}pz)\}_{8+14+9}$ or $SO_4^{2-} \subset \{cis\text{-}Cu^{II}(\mu\text{-}OH)(\mu\text{-}pz)\}_{31}$, respectively. As used herein, the symbol c means that the anion which precedes the symbol is encapsulated within the ring structure which is annotated after the symbol.

One example of a suitable counterion for forming the lid over the sulfate-encapsulating host assemblies is $Bu_4N^+$, resulting in anion-encapsulating aggregates $(Bu_4N)_2[SO_4^{2-} \subset \{cis\text{-}Cu^{II}(\mu\text{-}OH)(\mu\text{-}pz)\}_{6+12+10}]$ and $(Bu_4N)_2[SO_4^{2-} \subset \{cis\text{-}Cu^{II}(\mu\text{-}OH)(\mu\text{-}pz)\}_{8+14+9}]$ in the above example.

The unusually high solubility of $(Bu_4N)_2[SO_4^{2-} \subset \{cis\text{-}Cu^{II}(\mu\text{-}OH)(\mu\text{-}pz)\}_{6+12+10}]$, and $(Bu_4N)_2[SO_4^{2-} \subset \{cis\text{-}Cu^{II}(\mu\text{-}OH)(\mu\text{-}pz)\}_{8+14+9}]$ (>20 g in 100 ml $CH_2Cl_2$), as well as their solubility in non-polar solvents (such as $CS_2$, $CCl_4$ and benzene), indicate the existence of these hydrophobic nano-jars in solution (similar to the ones seen in the crystal structure), resulting from the association of the sulfate-encapsulating nano-jars 10 with the $Bu_4N^+$ "lids" 14 as shown in FIGS. 3 and 4.

Preliminary selectivity studies indicate a marked preference of the $[cis\text{-}Cu^{II}(\mu\text{-}OH)(\mu\text{-}pz)]_n$ assemblies of Host 1 and Host 2 described herein for the sulfate anion over nitrate or perchlorate anions. A self-assembly reaction using a 1:54 molar ratio of sulfate and nitrate (or perchlorate) anions led to the quantitative encapsulation of sulfate into the product, as determined gravimetrically by precipitation as $BaSO_4$ after digestion with 6M HCl. The preference for the anion with larger free energy of hydration ($SO_4^{2-}$:−1090 kJ/mol; $NO_3^-$:−306 kJ/mol; $ClO_4^-$:−214 kJ/mol) is known as anti-Hofmeister bias, and indicates that the normally observed Hofmeister bias does not control the encapsulation reaction. The selectivity for sulfate over nitrate, along with the stability at high (basic) pH is especially relevant for the sulfate-extraction efforts during nuclear waste treatment by vitrification, because it allows liquid-liquid extraction. The methods described herein also offer the benefit of recyclability of the sulfate-encapsulating assemblies. The encapsulating host assemblies can be recovered by stirring the dry residue obtained after $BaSO_4$ precipitation (containing $CuCl_2$, Hpz and $Et_3NHCl$) with excess $Et_3N$ in DMF. Following such mixing, the characteristic absorption at 599 nm indicates the re-assembly of the $[cis\text{-}Cu^{II}(\mu\text{-}OH)(\mu\text{-}pz)]_n$ rings.

To use Host 1 and Host 2 for sulfate extraction, a solvent, the stoichiometrically required amounts (based on the amount of sulfate to be extracted) of nano-jar ingredients of copper salt, a base (or copper hydroxide in place of the copper salt and base) and pyrazole, and a counterion contributor (if the base does not act as a counterion contributor) are combined with an aqueous solution containing sulfate ions, which may or may not be in the presence of competing ions such as nitrate, to form an organic-aqueous mixture, as described above. In other words, for sulfate extraction, a solvent, a copper contributor, a hydroxide contributor, a counterion contributor, and pyrazole are combined with the aqueous solution containing the targeted sulfate anions to form the organic-aqueous mixture. The copper contributor, hydroxide contributor and counterion contributor may be three separate compounds, or one compound may perform as a contributor of more than one of copper, hydroxide and counterions.

The components in the organic-aqueous mixture are permitted to react, after which the sulfate is encapsulated into the Host 1 and Host 2 ring assemblies, which are found in the organic phase of the organic-aqueous mixture. The organic layer of organic-aqueous mixture can then be separated from the aqueous layer using known separation techniques, such as the use of a separatory funnel.

Alternatively, to use Host 1 and Host 2 for sulfate extraction, a solvent, a polymer chain of $[Cu^{II}(\mu\text{-}OH)(\mu\text{-}pz)]_\infty$ and a counterion contributor are combined with an aqueous solution containing sulfate ions to form an organic-aqueous mixture, as described above. The components in the organic-aqueous mixture are permitted to react, after which the sulfate is encapsulated into the Host 1 and Host 2 ring assemblies, which are found in the organic phase of the organic-aqueous mixture. The organic layer of organic-aqueous mixture can then be separated from the aqueous layer using known separation techniques, such as the use of a separatory funnel.

In experiments, an aqueous solution containing 5 M nitrate ($NaNO_3$), 0.044 M sulfate ($Na_2SO_4$) and 1.25 M NaOH (pH 14), in which the sulfate to nitrate ratio is 1:114 was combined together with an organic phase containing the stoichiometrically (based on the amount of sulfate) required amounts of nano-jar components. The solution effectively and selectively extracted the sulfate anions from the aqueous phase to the organic phase, where they were encapsulated in the Host 1 and Host 2 "nano-jars." Sulfate extraction can also be performed at high dilutions, such as 20 mg of sulfate per liter, using toluene as a solvent.

Host 1 and Host 2 can be prepared on large scale via either depolymerisation of $[Cu^{II}(\mu\text{-}OH)(\mu\text{-}pz)]_\infty$ or a one-pot self-assembly reaction from its basic constituents in the presence of a sulfate ion.

Production of Host 1 and Host 2 via depolymerisation of $[Cu^{II}(\mu\text{-}OH)(\mu\text{-}pz)]_\infty$ includes the steps of combining aqueous solutions of $CuSO_4$ and KOH/Hpz (1:2:1 molar ratio), which results in the formation of a blue-purple precipitate (Scheme 1). The insolubility of this material in all common organic solvents, including refluxing pyridine (b.p.=115° C.) and DMF (b.p.=153° C.), suggests a polymeric structure. Elemental analysis results concur with the formula [Cu(OH)(pz)] (for $C_3H_4CuN_2O$, M.W.=147.62, calculated/found: C, 24.41 24.25%; H, 2.73/2.72%; N, 18.98 18.40%). The structure of this intractable material likely consists of linear polymeric chains resulting from an all-trans arrangement of the pyrazole and OH moieties about the copper centers, similar to the ones found in $[Cu^{II}(\mu\text{-}pz)_2]_\infty$.

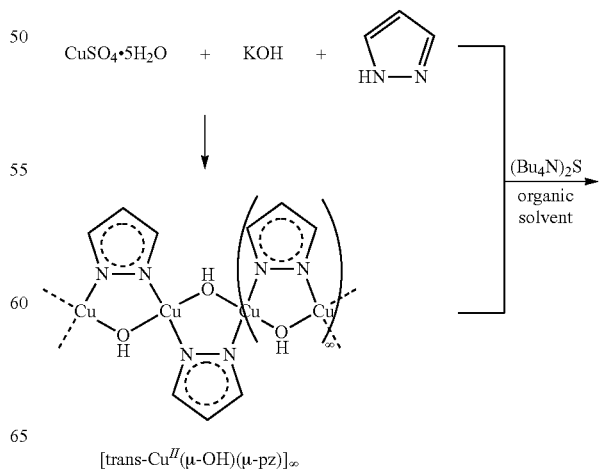

-continued

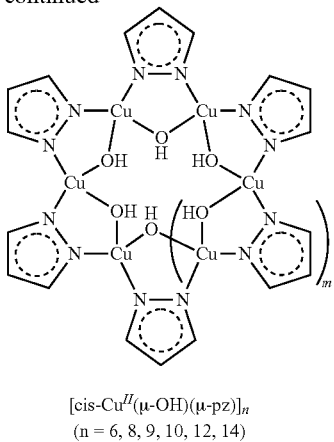

[cis-Cu$^{II}$(μ-OH)(μ-pz)]$_n$
(n = 6, 8, 9, 10, 12, 14)

(Bu$_4$N)HSO$_4$ or (Bu$_4$N)$_2$SO$_4$ can be added to a suspension of [Cu(μ-OH)(μ-pz)]$_\infty$ in THF or toluene, which leads to the immediate formation of a deep blue solution, and gradual dissolution of the solid. Evaporation of the solvent produces a dark blue powder, which is highly soluble in a wide variety of solvents (including CCl$_4$, CS$_2$, aromatic hydrocarbons, ethers, ketones, esters, nitriles, amines, halogenated and nitro compounds, DMF and DMSO), slightly soluble in alcohols, and insoluble in aliphatic hydrocarbons and water. In CH$_2$Cl$_2$ or DMF solution, it exhibits an absorption maximum at 599 nm, virtually identical to the one of [Cu(NH$_3$)$_4$(H$_2$O)$_2$]$^{2+}$ in H$_2$O (600 nm), and a molar absorptivity of ~2.9×10$^3$ L mol$^{-1}$ cm$^{-1}$. Hexane vapor diffusion to a toluene solution is then used to obtain dark blue single crystals in the form of blocks and thin plates. X-ray diffraction analysis revealed their structures to be (Bu$_4$N)$_2$[SO$_4^{2-}$ ⊂ {cis-Cu$^{II}$(μ-OH)(μ-pz)}$_{28}$], and (Bu$_4$N)$_2$[SO$_4^{2-}$ ⊂ {cis-Cu$^{II}$(μ-OH)(μ-pz)}$_{31}$], respectively.

To synthesize Host 1 and Host 2 via a direct self-assembly reaction, several potential self-assembly reactions are possible. As a first option, the constituents of CuSO$_4$.5H$_2$O, KOH, Hpz and (Bu$_4$N)$_2$SO$_4$ (28:56:28:1 molar ratio) can be added to various solvents (THF, CH$_2$Cl$_2$ or DMF). Alternatively, CuSO$_4$.5H$_2$O, KOH, pyrazole and Bu$_4$NOH (in water) can be combined in a THF solution and mixed to form a solution, from which the product can be separated upon filtration and evaporation of the solvent. Alternatively, a solution of CuSO$_4$.5H$_2$O in DMF can be combined with a solution of KOH, pyrazole and Bu$_4$NOH (in water) in methanol, and the resulting solution poured into water, to produce a precipitate of the product. Alternatively, CuSO$_4$.5H$_2$O, KOH, pyrazole and Bu$_4$NOH (in water) can be added to CH$_2$Cl$_2$, to produce a solution, from which the product can be separated upon filtration and evaporation of the solvent. The product in each of these cases includes (Bu$_4$N)$_2$[SO$_4^{2-}$ ⊂ {cis-Cu$^{II}$(μ-OH)(μ-pz)}$_{28}$] and (Bu$_4$N)$_2$[SO$_4^{2-}$ ⊂ {cis-Cu$^{II}$(μ-OH)(μ-pz)}$_{31}$], as evidenced by mass spectrometric analysis (electrospray ionization).

(Bu$_4$N)$_2$[SO$_4^{2-}$ ⊂ {cis-Cu$^{II}$(μ-OH)(μ-pz)}$_{28}$] can also be crystallized from chlorobenzene, 1,2-dichloroethane or n-butylamine by hexane vapor diffusion, and from CH$_2$Cl$_2$ by Et$_2$O vapor diffusion. SO$_4^{2-}$ ⊂ {cis-Cu$^{II}$(μ-OH)(μ-pz)}$_{31}$ can also be crystallized as the Bu$_4$N-salt from chlorobenzene. Moreover, crystals of (Bu$_4$N)$_2$[SO$_4^{2-}$ ⊂ {cis-Cu$^{II}$(μ-OH)(μ-pz)}$_{28}$] were also obtained by recrystallization from boiling n-butanol (b.p.=118° C.), indicating stability of the rings at that temperature.

Addition of the various counterions (e.g., 18-crown-6, Et$_3$N) results in the formation of nano-jars with alternate "lids." For example, CuSO$_4$.5H$_2$O, KOH, pyrazole and 18-crown-6 (28:56:28:2 molar ratio) can be added to THF to produce (K$^+$ ⊂ 18-crown-6)$_2$[SO$_4^{2-}$ ⊂ {cis-Cu$^{II}$(μ-OH)(μ-pz)}$_{28}$], and (K$^+$ ⊂ 18-crown-6)$_2$[SO$_4^{2-}$ ⊂ {cis-Cu$^{II}$(μ-OH)(μ-Pz)}$_{31}$]. These nano-jars form in the organic solution, and can be isolated by evaporation of the solvent or, in the case of organic solvents which are miscible with water, by the addition of water to form a precipitate of the product. SO$_4^{2-}$ ⊂ {cis-Cu$^{II}$(μ-OH)(μ-pz)}$_{31}$ can also be crystallized as the K$^+$18-crown-6-salt from n-butyl acetate, by hexane vapor diffusion. Alternatively, CuSO$_4$.5H$_2$O, pyrazole and Et$_3$N (1:1:2 molar ratio) can be added to DMF, to produce a precipitate of (Et$_3$NH)$_2$[SO$_4^{2-}$ ⊂ {cis-Cu$^{II}$(μ-OH)(μ-pz)}$_{28}$] and (Et$_3$NH)$_2$[SO$_4^{2-}$ ⊂ {cis-Cu$^{II}$(μ-OH)(μ-Pz)}$_{31}$] (in quantitative yield) upon addition of water.

The counterions and solvents used apparently have no influence on the self-assembly process of the anion-encapsulating host, since only {cis-Cu$^{II}$(μ-OH)(μ-pz)}$_{28}$ and {cis-Cu$^{II}$(μ-OH)(μ-pz)}$_{31}$ resulted from those reactions. Running the reaction without a suitable counterion (e.g., using CuSO$_4$.5H$_2$O, KOH and Hpz only), however, led to an insoluble material.

Figure 5:
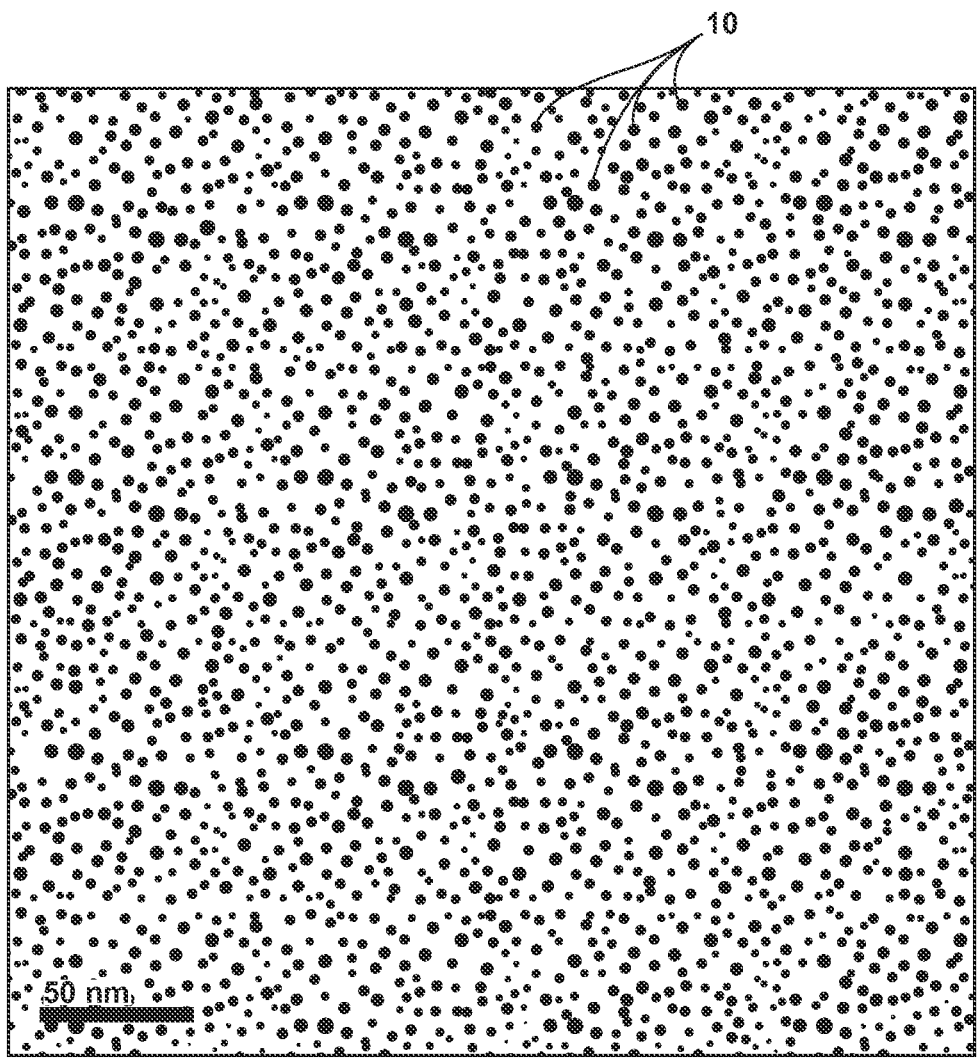
FIG. 5 is a transmission electron micrograph (TEM) image of sulfate encapsulating assemblies deposited onto a copper grid by the evaporation of a solution in ethanol.

Host 1 and Host 2 are both formed during the synthesis steps described herein, and coexist in the same solution. Host 1 and Host 2 can be separated upon crystallization due to the visual differences in the crystals (Host 1 forms dark blue prismatic crystals and Host 2 forms dark purple-blue plate-like crystals). FIG. 5 includes a transmission electron micrograph (TEM) image of sulfate encapsulating assemblies, or nano-jars 10, deposited onto a copper grid by the evaporation of a solution in ethanol showing the crystals. Other synthesis procedures may allow for the preferential formation of one of Host 1 or Host 2. However, as both are well suited to sulfate ion extraction, coexistence in the same solution does not negatively impact the selective extraction of sulfate ions.

Figure 8:
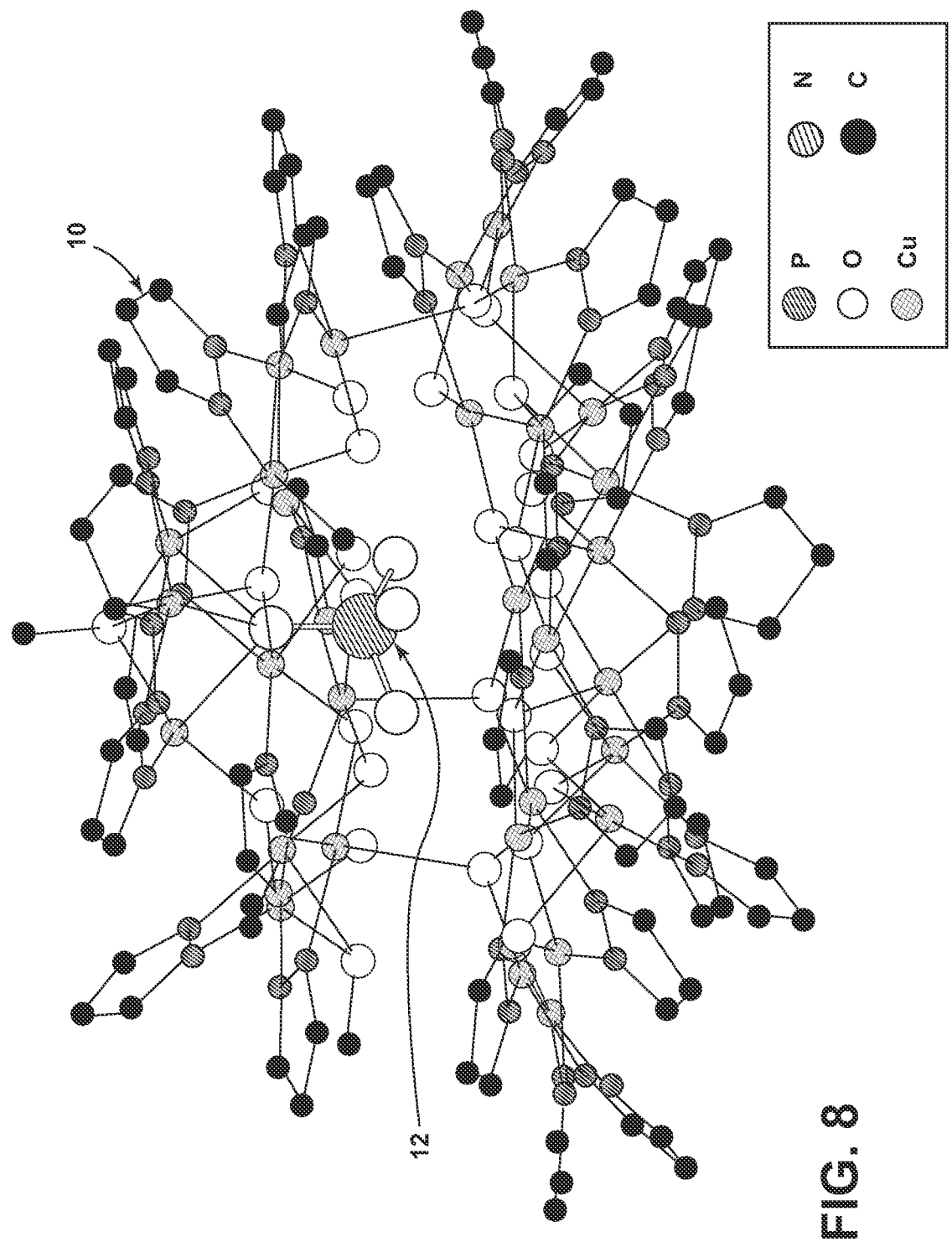
FIG. 8 is a side plan view of the phosphate encapsulating assembly, where H atoms are omitted for clarity.

Another preferred embodiment of an anion-encapsulating aggregate is based on the four-ring {cis-Cu$^{II}$(μ-OH)(μ-pz)}$_{6+12+9}${Cu$^{II}_3$(μ$_3$-OH)(μ-pz)$_3$} encapsulating host assembly ("Host 3"). Host 3 can also be denoted as {cis-Cu$^{II}_{30}$(μ-OH)$_{28}$(μ-pz)$_{30}$}, and is one ring set that is representative of {cis-Cu$^{II}_{30}$(μ-OH)$_{28}$(μ-pz)$_{30}$}. Host 3 shows selectivity for the encapsulation of phosphate and arsenate anions from a solution containing competing ions where the competing ions would normally be favored for extraction into an organic phase by the Hofmeister bias. Host 3, like Hosts 1 and 2, results in the wrapping of the target ions 12 within a nano-jar structure 10, which selectively binds the targeted anions, as shown in FIG. 8.

As with the separation methods for sulfates described above, to selectively separate phosphate or arsenate anions from an aqueous solution, a solvent, the components stoichiometrically (based on the amount of phosphate and/or arsenate) necessary to create the Host 3 nano-jar, and a counterion contributor (if the base does not act as such) are combined with the aqueous solution containing the target anions to form an organic-aqueous mixture that has an overall neutral or basic pH level, and the combined components are permitted to react. Upon such reaction, the nano-jars self-assemble around the target anions and transfer into the organic phase, selectively removing phosphate or arsenate from the aqueous phase, even in the presence of other anions which would be favored by the Hofmeister bias.

Alternatively, a solvent, a polymeric chain of [Cu$^{II}$(μ-OH)(μ-pz)]$_\infty$ and a counterion contributor can be combined with an aqueous solution containing the targeted anion for extraction to form an organic-aqueous mixture with an overall neutral or basic pH level, and permitted to react. Upon such reaction, the nano-jars self-assemble around the target anions and transfer into the organic phase, selectively removing phosphate or arsenate from the aqueous phase. Separation of the organic phase and aqueous solution results in extraction of some or all of the targeted anions from the aqueous solution, even in the presence of other anions which would be favored by the Hofmeister bias.

To synthesize Host 3, several methods may be employed. First, $Cu(OH)_2$ can be prepared by mixing aqueous solutions of $CuSO_4 \cdot 5H_2O$ with KOH 85%. A precipitate forms, which is preferably washed with water and then THF and dried. The dried solid can then be added to a solution of pyrazole and tetrabutylammonium phosphate in tetrahydrofuran, forming a solution with a deep blue color. Upon filtration and evaporation, a dark blue powder is obtained, containing a four ring (3, 6, 9 and 12 Cu-pyrazole rings) encapsulating host assembly encapsulating phosphate anions of the formula $(Bu_4N)[PO_4^{3-} \subset \{cis\text{-}Cu^{II}(\mu\text{-}OH)(\mu\text{-}pz)\}_{6+12+9}\{Cu^{II}_3(\mu_3\text{-}OH)(\mu\text{-}pz)_3\}]$ or $(Bu_4N)[PO_4^{3-} \subset \{cis\text{-}Cu^{II}_{30}(\mu\text{-}OH)_{28}(\mu\text{-}pz)_{30}\}]$. The same encapsulating host assembly can be synthesized in the presence of an arsenate ion, to encapsulate the arsenate ion rather than the phosphate ion, resulting in $(Bu_4N)[AsO_4^{3-} \subset \{cis\text{-}Cu^{II}(\mu\text{-}OH)(\mu\text{-}pz)\}_{6+12+9}\{Cu^{II}_3(\mu_3\text{-}OH)(\mu\text{-}pz)_3\}]$ or $(Bu_4N)[AsO_4^{3-} \subset \{cis\text{-}Cu^{II}_{30}(\mu\text{-}OH)_{28}(\mu\text{-}pz)_{30}\}]$.

In a laboratory scale synthesis, a solution of 968 mg $CuSO_4 \cdot 5H_2O$ in 20 mL $H_2O$ was mixed with a solution of 512 mg KOH 85% in 20 ml $H_2O$. The precipitate that formed upon mixing was washed extensively with water, and then with THF. The dried precipitate was then added to a solution of 264 mg pyrazole and 200 mg tetrabutylammonium phosphate in 15 ml tetrahydrofuran. After stirring for 2 days, the deep blue solution was filtered and the solvent was evaporated. 684 mg dark blue powder was obtained.

Another method of synthesis of Host 3 includes combining $Cu_2(OH)(PO_4)$, KOH 85%, pyrazole and $Bu_4NOH$ solution (1 M in water) and stirring, to form a solution. Upon filtration and evaporation of the solution, a dark blue powder containing $(Bu_4N)[PO_4^{3-} \subset \{cis\text{-}Cu^{II}_{30}(\mu\text{-}OH)_{28}(\mu\text{-}pz)_{30}\}]$ was obtained.

In a laboratory scale synthesis, 464 mg $Cu_2(OH)(PO_4)$, 356 mg KOH 85%, 264 mg pyrazole and 460 mg $Bu_4NOH$ solution (1 M in water) were stirred together for 2 days. The deep blue solution which formed was filtered and the solvent was evaporated. 548 mg dark blue powder was obtained.

Another method of synthesis of Host 3 includes dissolving $Cu(NO_3)_2 \cdot 2.5H_2O$ in dimethylformamide, and then adding a solution of NaOH, pyrazole, $H_3PO_4$ 85% and $Bu_4NOH$ solution (1 M in water) in methanol under vigorous stirring. After stirring, the solution is added to water, forming a precipitate. The precipitate can be filtered out of solution, washed with water, and dried in an oven, forming a dark blue powder containing $(Bu_4N)[PO_4^{3-} \subset \{cis\text{-}Cu^{II}_{30}(\mu\text{-}OH)_{28}(\mu\text{-}pz)_{30}\}]$.

In a laboratory scale synthesis 5.000 g $Cu(NO_3)_2 \cdot 2.5H_2O$ was dissolved in 167 ml dimethylformamide. A solution of 1.720 g NaOH, 1.464 g pyrazole, 83 mg $H_3PO_4$ 85% and 0.72 ml $Bu_4NOH$ solution (1 M in water) in 33 ml methanol was added in 1-2 ml portions under vigorous stirring. After stirring for 3 days, the solution was poured into 500 ml water. The precipitate was filtered out, washed with water and dried in an oven at 80° C. 3.727 g dark blue powder was obtained.

Another method of synthesis of Host 3 includes the steps of reacting $[Cu(\mu\text{-}OH)(\mu\text{-}pz)]_\infty$ polymer with a solution of tetrabutylammonium phosphate in chlorobenzene. The solution is then filtered, and the solvent evaporated, to obtain a dark blue powder containing $(Bu_4N)[PO_4^{3-} \subset \{cis\text{-}Cu^{II}_{30}(\mu\text{-}OH)_{28}(\mu\text{-}pz)_{30}\}]$.

In a laboratory scale synthesis 500 mg $[Cu^{II}(\mu\text{-}OH)(\mu\text{-}pz)]_\infty$ polymer was refluxed with 200 mg tetrabutylammonium phosphate in 15 ml chlorobenzene for 2 hours. The solution was filtered and the solvent was evaporated. 430 mg dark blue powder was obtained.

Figure 7:
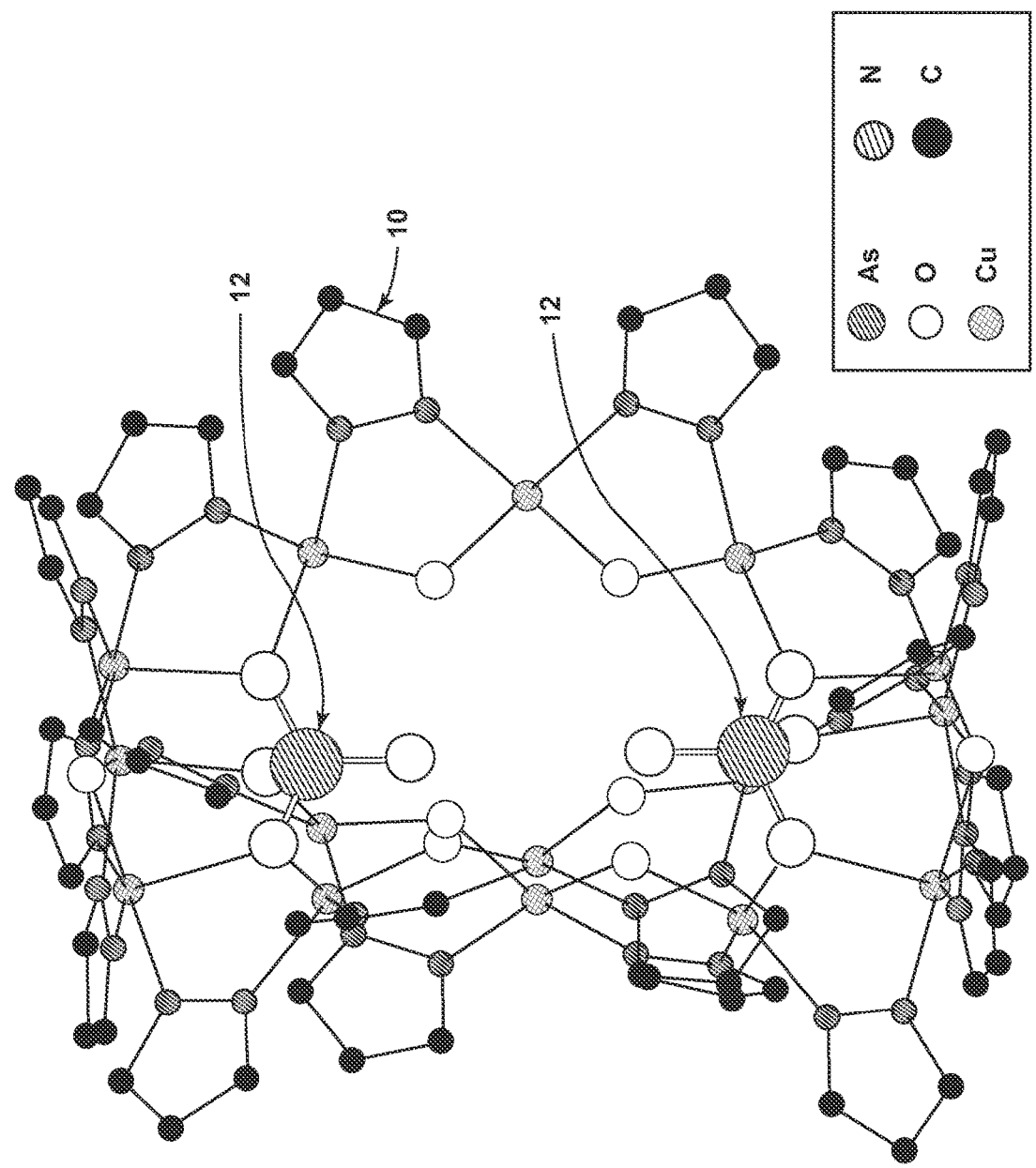
FIG. 7 is a side plan view of an arsenate-encapsulating compound, where H atoms are omitted for clarity.

Another preferred anion-encapsulating aggregate is based on the $Cu_{15}$ compound, a $\{Cu^{II}_3(\mu_3\text{-}OH)(\mu\text{-}pz)_3\}_2\{Cu^{II}_3(\mu\text{-}OH)_2(\mu\text{-}pz)_4\}_3$ host assembly ("Host 4"), which selectively encapsulates two phosphate or two arsenate anions, as shown in FIG. 7. Host 4 can also be denoted as $\{cis\text{-}Cu^{II}_{15}(\mu\text{-}OH)_7(\mu\text{-}pz)_{18}\}$, and is one ring set that is representative of $\{cis\text{-}Cu^{II}_{15}(\mu\text{-}OH)_7(\mu\text{-}pz)_{18}\}$. Host 4 is formed at the same time and in the same reactions as Host 3, as described above, and is present when phosphate or arsenate are present in the aqueous solution for extraction.

As with the separation methods described above, when selectively separating phosphate or arsenate anions from an aqueous solution, a solvent, the components necessary to create the Host 4 compound, and a counterion contributor (if the base does not act as such) are combined with the aqueous solution containing the target anions to form an organic-aqueous mixture with an overall neutral or basic pH level, and the combined components are permitted to react. Upon such reaction, the compounds comprising Host 4 self-assemble around the target anions and transfer into the organic phase, selectively removing phosphate and/or arsenate anions from the aqueous phase, even in the presence of other anions which would be favored by the Hofmeister bias.

Alternatively, a solvent, a polymeric chain of $[Cu^{II}(\mu\text{-}OH)(\mu\text{-}pz)]_\infty$ and a counterion contributor can be combined with an aqueous solution containing the targeted anion for extraction to form an organic-aqueous mixture with an overall neutral or basic pH level and permitted to react. Upon such reaction, the Host 4 compound self-assembles around the target anions and transfers into the organic phase, selectively removing phosphate or arsenate from the aqueous phase. Separation of the organic phase and aqueous solution results in extraction of some or all of the targeted anions from the aqueous solution, even in the presence of other anions which would be favored by the Hofmeister bias.

One method of synthesizing Host 4 is to react $Cu(OH)_2$ with a solution of pyrazole, $Bu_4NOH$ (1M in water) and $Na_2HAsO_4 \cdot 7H_2O$ in an organic solvent, such solvents including, without limitation solvents such as methylene chloride, tetrahydrofuran or dimethylformamide). The solution is then filtered, and the solvent evaporated, to obtain a dark blue powder containing $(Bu_4N)_2[(AsO_4^{3-})_2^- \subset \{cis\text{-}Cu^{II}_{15}(\mu\text{-}OH)_7(\mu\text{-}pz)_{18}\}]$.

In a laboratory scale synthesis, a solution of 968 mg of $CuSO_4 \cdot 5H_2O$ dissolved in 50 mL of water and 512 mg KOH (pellets, 85%) dissolved in 50 mL of water were combined and mixed to form a powder of $Cu(OH)_2$. After washing thoroughly with water and then tetrahydrofuran, the copper hydroxide powder was added to a solution of 264 mg pyrazole, 0.415 ml $Bu_4NOH$ (1M in $H_2O$) and 86 mg sodium arsenate ($Na_2HAsO_4 \cdot 7H_2O$) in 15 ml of tetrahydrofuran, and stirred for 24 hours. The deep blue solution was filtered and the solvent removed.

The same procedure as that described above can be used for the synthesis of Host 4 with a phosphate ion encapsulated therein, by substituting tetrabutylammonium phosphate for the Bu$_4$NOH and Na$_2$HAsO$_4$.7H$_2$O, resulting in an aggregate containing (Bu$_4$N)$_2$[(PO$_4$$^{3-}$)$_2$ ⊂ {Cu$^{II}$$_3$($\mu_3$-OH)($\mu$-pz)$_3$}$_2${Cu$^{II}$$_3$($\mu$-OH)$_2$($\mu$-pz)$_4$}$_3$] or (Bu$_4$N)$_2$[(PO$_4$$^{3-}$)$_2$ ⊂ {cis-Cu$^{II}$$_{15}$($\mu$-OH)$_7$($\mu$-pz)$_{18}$}].

If phosphate and arsenate are both contained within the aqueous solution, they will both be extracted by Host 3 and Host 4, as described herein.

Another preferred anion-encapsulating aggregate is based on the four-ring {cis-Cu$^{II}$($\mu$-OH)($\mu$-pz)}$_{6+12+12+6}$ encapsulating host assembly ("Host 5"). Host 5 can also be denoted as {cis-Cu$^{II}$($\mu$-OH)($\mu$-pz)}$_{36}$, and is one ring set that is representative of {cis-Cu$^{II}$($\mu$-OH)($\mu$-pz)}$_{36}$. Host 5 shows selectivity for the encapsulation of chloride anions from a solution containing competing ions, where the competing ions would normally be favored by the Hofmeister bias. Host 5, like previous hosts discussed herein, results in the wrapping of target ions within a nano-jar structure, which selectively binds the targeted anions.

As with the separation methods described above, to selectively separate chloride anions from an aqueous solution, a solvent, the components stoichiometrically (based on the amount of chloride) necessary to create the Host 5 nano-jar, and a counterion contributor (if the base does not act as such) are combined with the aqueous solution containing the target anions to form an organic-aqueous mixture with an overall neutral or basic pH level, and the combined components are permitted to react. Upon such reaction, the nano-jars self-assemble around the target anions and transfer into the organic phase, selectively removing chloride ions from the aqueous phase, even in the presence of other anions which would be favored by the Hofmeister bias.

Alternatively, a solvent, a polymeric chain of [Cu$^{II}$($\mu$-OH)($\mu$-pz)]$_\infty$ and a counterion contributor can be combined with an aqueous solution containing the targeted anion for extraction to form an organic-aqueous mixture with an overall neutral or basic pH level, and permitted to react. Upon such reaction, the nano-jars self-assemble around the target anions and transfer in to the organic phase, selectively removing the chloride from the aqueous phase. Separation of the organic phase and aqueous phase solution results in extraction of some or all of the targeted anions from the aqueous solution, even in the presence of other anions which would be favored by the Hofmeister bias.

To synthesize Host 5, several methods may be employed. First, Cu(OH)$_2$ can be prepared by mixing aqueous solutions of CuSO$_4$.5H$_2$O and NaOH. A precipitate of Cu(OH)$_2$ forms, which is preferably collected from the solution on a filter, washed with water and then washed with tetrahydrofuran. The Cu(OH)$_2$ is then dried and added to a solution of pyrazole and Bu$_4$NCl in THF, forming a solution with a deep blue color. Upon filtration and evaporation, deep blue crystals of the formula (Bu$_4$N)[Cl$^-$ ⊂ {cis-Cu$^{II}$($\mu$-OH)($\mu$-pz)}$_{36}$] were obtained by re-crystallization from CH$_2$Cl$_2$/Et$_2$O.

In a laboratory synthesis, a solution of 968 mg CuSO$_4$.5H$_2$O in 15 ml H$_2$O was combined with a solution of 310 mg NaOH in 10 ml H$_2$O. A blue precipitate formed and was collected on a fritted glass filter. The precipitate was washed 3 times with H$_2$O and then with tetrahydrofuran. To the dry Cu(OH)$_2$ residue, a solution of 264 mg pyrazole and 100 mg Bu$_4$NCl in 15 ml THF was added. After stirring overnight, the clear deep blue solution was filtered and the solvent removed under vacuum. Deep blue crystals suitable for X-ray diffraction were obtained by recrystallization from CH$_2$Cl$_2$/Et$_2$O.

Another method of synthesis of Host 5 includes dissolving CuCl$_2$.2H$_2$O in dimethylformamide, and then adding a solution of KOH, pyrazole and Bu$_4$NOH solution (1 M in water) in methanol under vigorous stirring. After stirring, the solution can be filtered, and the solvent evaporated. The residue can be dissolved in CH$_2$Cl$_2$. Upon filtration and evaporation of the residue in CH$_2$Cl$_2$ solution, a dark blue powder of the formula (Bu$_4$N) [Cl$^-$ ⊂ {cis-Cu$^{II}$($\mu$-OH)($\mu$-pz)}$_{36}$] is obtained.

In a laboratory scale synthesis, 4.262 g CuCl$_2$.2H$_2$O was dissolved in 150 ml dimethylformamide. A solution of 3.255 g KOH 85%, 1.702 g pyrazole and 720 mg Bu$_4$NOH solution (1 M in water) in 30 ml methanol was added in 1-2 ml portions under vigorous stirring. After stirring for one day, the solution was filtered and the solvent was evaporated. The residue was dissolved in CH$_2$Cl$_2$, the solution was filtered and the solvent was evaporated. 3.914 g dark blue powder was obtained.

Additional preferred embodiments of anion-encapsulating aggregates are based on the three-ring {cis-Cu$^{II}$($\mu$-OH)($\mu$-pz)}$_{7+13+9}$ encapsulating host assembly ("Host 6"), {cis-Cu$^{II}$($\mu$-OH)($\mu$-pz)}$_{8+13+8}$ encapsulating host assembly ("Host 7"), and {cis-Cu$^{II}$($\mu$-OH)($\mu$-pz)}$_{6+12+9}$ encapsulating host assembly ("Host 8"). Hosts 6 and 7 can also be denoted as {cis-Cu$^{II}$($\mu$-OH)($\mu$-pz)}$_{29}$, while Host 8 can be denoted as {cis-Cu$^{II}$($\mu$-OH)($\mu$-pz)}$_{27}$. Each of Hosts 6 and 7 is a ring set that is representative of {cis-Cu$^{II}$($\mu$-OH)($\mu$-pz)}$_{29}$, and Host 8 is a ring set that is representative of {cis-Cu$^{II}$($\mu$-OH)($\mu$-pz)}$_{27}$. Hosts 6, 7, and 8 show selectivity for the encapsulation of carbonate atoms from a solution containing competing ions where the competing ions would normally be favored for extraction into an organic phase by the Hofmeister bias. Hosts 6, 7 and 8, like the previously described hosts, result in the wrapping of target ions in a nano-jar structure, which selectively binds the targeted anions.

As with the separation methods for sulfates described above, to selectively separate carbonate anions from an aqueous solution, a solvent, the components stoichiometrically (based on the amount of carbonate) necessary to create the Host 6, Host 7 and/or Host 8 "nano-jars," and a counterion contributor (if the base does not act as such) are combined with the aqueous solution containing the target anions to form an organic-aqueous mixture that has an overall neutral or basic pH level, and the combined components are permitted to react. Upon such reaction, the nano-jars self-assemble around the target anions and transfer into the organic phase, selectively removing carbonate anions from the aqueous phase, even in the presence of other anions which would be favored by the Hofmeister bias.

Alternatively, a solvent, a polymeric chain of [Cu$^{II}$($\mu$-OH)($\mu$-pz)]$_\infty$ and a counterion contributor are combined with an aqueous solution containing the targeted anion for extraction to form an organic-aqueous mixture that has an overall neutral or basic pH level, and are permitted to react. Upon such reaction, the nano-jars self-assemble around the target anions and transfer into the organic phase, selectively removing carbonate from the aqueous phase. Separation of the organic phase and aqueous solution results in extraction of some or all of the targeted anions from the aqueous solution, even in the presence of other anions which would be favored by the Hofmeister bias.

To synthesize Hosts 6, 7 and 8, Cu(OH)$_2$ can be prepared by mixing aqueous solutions of CuSO$_4$.5H$_2$O and KOH 85%. A precipitate forms, which is preferably washed with water and then THF and dried. The dried solid can then be added to a solution of pyrazole and tetrabutylammonium hydroxide in tetrahydrofuran, forming a solution with a deep blue color. Additional CO$_2$, such as in the form of dry ice, can be added to the solution. CO$_2$ from air will also serve as carbonate source. Upon filtration and evaporation, a dark blue powder containing $(Bu_4N)_2[CO_3^{2-} \subset \{cis\text{-}Cu^{II}(\mu\text{-}OH)(\mu\text{-}pz)\}_{29}]$ and $(Bu_4N)_2[CO_3^{2-} \subset \{cis\text{-}Cu^{II}(\mu\text{-}OH)(\mu\text{-}pz)\}_{27}]$ is obtained.

In a laboratory scale synthesis, $Cu(OH)_2$ was prepared by mixing aqueous solutions of 968 mg $CuSO_4.5H_2O$ in 20 ml $H_2O$ with 512 mg KOH 85% in 20 ml $H_2O$. The precipitate was washed extensively with water, and then with THF. The dried solid was added to a solution of 264 mg pyrazole and 270 mg $Bu_4NOH$ solution (1 M in water) in 15 ml tetrahydrofuran. A few pieces of dry ice ($CO_2$) were added to this solution, and it was stirred for one day. The deep blue solution was filtered and the solvent was evaporated. 629 mg dark blue powder was obtained.

As with the formation of Host 1 and Host 2, all three of the ring combinations described as Hosts 6, 7 and 8 are formed during the synthesis steps described herein, and coexist in the same solution. Other synthesis procedures may allow for the preferential formation of one of Hosts 6, 7 or 8. However, as all three are well suited to carbonate ion extraction, coexistence in the same solution does not negatively impact the selective extraction of carbonate ions.

Figure 6:
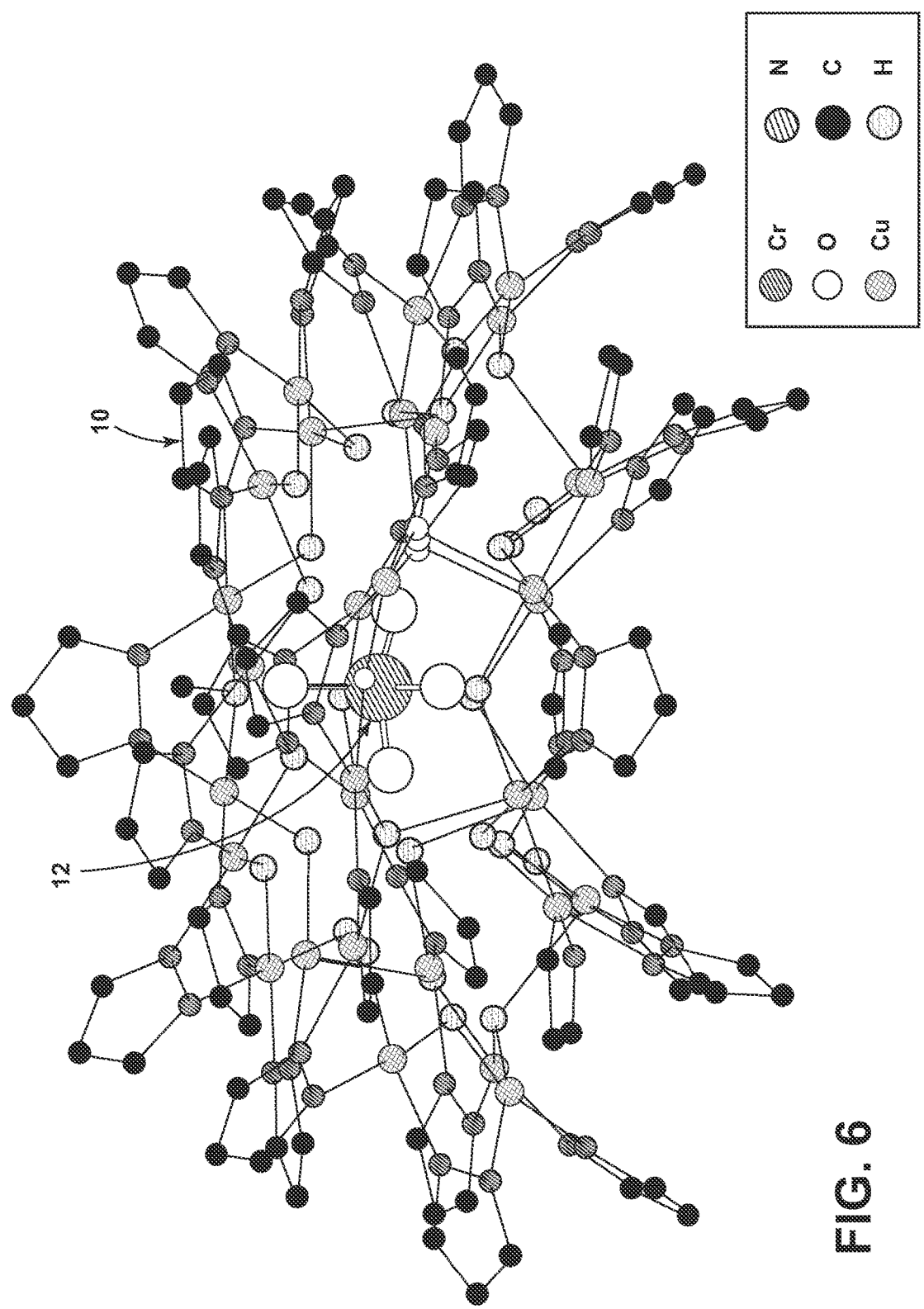
FIG. 6 is a side plan view showing the formation of the chromate-encapsulating "nano-jar"

Host 2, described above, also permits the selective extraction of chromate from aqueous solution, according to the same principles and procedures as described above with relation to sulfate and other target anions. FIG. 6 illustrates the encapsulation of chromate in the chromate-encapsulating assembly.

With respect to the production of lids for the nano-jars described herein, during formation of the nano-jars, smaller alkali or alkali earth metal cations can also be used as the lid-forming counterions for the preparation of $M_2[CO_3^{2-} \subset \{cis\text{-}Cu^{II}(\mu\text{-}OH)(\mu\text{-}pz)\}_{27}]^{2-}$, $M_2[CO_3^{2-} \subset \{cis\text{-}Cu^{II}(\mu\text{-}OH)(\mu\text{-}pz)\}_{29}]^{2-}$ and $M_2[CO_3^{2-} \subset \{cis\text{-}Cu^{II}(\mu\text{-}OH)(\mu\text{-}pz)\}_{31}]^{2-}$, where M is chosen from the group consisting of cesium, rubidium, potassium, sodium, and barium. The cesium, rubidium, potassium, sodium or barium may be added via hydroxides of these components. The products described below were identified by electrospray ionization mass spectrometry in an acetonitrile solution (ESI–: m/z 2780, 2984, and 3118).

For example, in a laboratory synthesis cesium was used to form the lid, as follows: 187 mg $Cu(NO_3)_2.2.5H_2O$ (0.804 mmol), 360 mg $CsOH.H_2O$ (containing ≤10% $Cs_2CO_3$) and 55 mg pyrazole (0.808 mmol) were added to 10 ml THF, and stirred for 3 days. A dark brown wet residue was removed from the deep blue solution by filtration and the solvent was evaporated to yield 128 mg of a dark blue powder.

In another laboratory scale synthesis, rubidium was used to form the lid. 187 mg $Cu(NO_3)_2.2.5H_2O$ (0.804 mmol), 250 mg $RbOH.H_2O$ (containing ≤15% $Rb_2CO_3$) and 55 mg pyrazole (0.808 mmol) were added to 10 ml THF, and stirred for 7 days. A dark brown wet residue was removed from the deep blue solution by filtration and the solvent was evaporated to yield 127 mg of a dark blue powder.

In another laboratory scale synthesis, potassium was used to form the lid. 342 mg $Cu(NO_3)_2.2.5H_2O$ (1.47 mmol), 194 mg KOH 85% (2.94 mmol), 100 mg pyrazole (1.47 mmol) and 15 mg $K_2CO_3$ (0.109 mmol) were added to 10 ml THF, and stirred for 3 days. A dark brown wet residue was removed from the deep blue solution by filtration and the solvent was evaporated to yield 219 mg of a dark blue powder.

In another laboratory scale synthesis, sodium was used to form the lid. 187 mg $Cu(NO_3)_2.2.5H_2O$ (0.804 mmol), 70 mg NaOH (1.75 mmol), 55 mg pyrazole (0.808 mmol) and 11 mg $Na_2CO_3.H_2O$ (0.0887 mmol) were added to 10 ml THF, and stirred for 4 days. A dark brown wet residue was removed from the deep blue solution by filtration and the solvent was evaporated to yield 82 mg of a dark blue powder.

In a final non-limiting example, barium was used to form the lid. In a laboratory scale synthesis 902 mg $Cu(NO_3)_2.2.5H_2O$ (3.88 mmol), 1.300 g $BaOH.8H_2O$ (containing ≤2% $BaCO_3$) and 264 mg pyrazole (3.88 mmol) were added to 25 ml THF, and stirred for 7 days. A light blue residue was removed from the deep blue solution by filtration and the solvent was evaporated to yield 629 mg of a dark blue powder.

Another preferred anion-encapsulating aggregate is based on the $\{cis\text{-}Cu^{II}(\mu\text{-}OH)(\mu\text{-}pz)\}_{27}$ encapsulating host assembly ("Host 9"), the $\{cis\text{-}Cu^{II}(\mu\text{-}OH)(\mu\text{-}pz)\}_{29}$ encapsulating host assembly ("Host 10"), and the $\{cis\text{-}Cu^{II}(\mu\text{-}OH)(\mu\text{-}pz)\}_{31}$ encapsulating host assembly ("Host 11"). Hosts 9, 10, and 11 show selectivity for the encapsulation of tetrafluoroberyllate ($BeF_4^{2-}$) anions. As with the separation methods described above, to selectively separate tetrafluoroberyllate anions from solution, a solvent, the components necessary to create the Host 9, 10, and 11 nano-jars, and a counterion contributor (if the base does not act as such) are combined with the aqueous solution containing the target anions to form an organic-aqueous mixture that has an overall neutral or basic pH level, and the combined components are permitted to react. Upon such reaction, the nano-jars self-assemble around the target anions and transfer into the organic phase, selectively removing tetrafluoroberyllate ions from the aqueous phase.

In a laboratory synthesis, 1.300 g $CuBeF_4.5H_2O$ (5.45 mmol), 432 mg NaOH (10.8 mmol), 371 mg pyrazole (5.45 mmol) and 356 mg $Bu_4NOH$ (1M in $H_2O$) (0.356 mmol) were added to 30 mL of THF and stirred for 3 days. A white solid was removed from the deep blue solution by filtration and the solvent was evaporated to yield 951 mg of a dark blue powder. The identity of the products was confirmed by electrospray ionization mass spectrometry in acetonitrile solution (ESI–: $[BeF_4^{2-} \subset \{cis\text{-}Cu^{II}(\mu\text{-}OH)(\mu\text{-}pz)\}_{27}]^{2-}$ m/z 2035, $[BeF_4^{2-} \subset \{cis\text{-}Cu^{II}(\mu\text{-}OH)(\mu\text{-}pz)\}_{28}]^{2-}$ m/z 2109, $[BeF_4^{2-} \subset \{cis\text{-}Cu^{II}(\mu\text{-}OH)(\mu\text{-}pz)\}_{29}]^{2-}$ m/z 2183, $[BeF_4^{2-} \subset \{cis\text{-}Cu^{II}(\mu\text{-}OH)(\mu\text{-}pz)\}_{31}]^{2-}$ m/z 2331.

Another process which allows the formation of a single anion-encapsulating aggregate involves including lead ions with copper in the presence of sulfate during the anion-encapsulating aggregate formation. Addition of lead ions to the copper salt, pyrazole, and base with the aqueous solution containing the anions to be extracted results in formation of primarily $\{cis\text{-}Cu^{II}(\mu\text{-}OH)(\mu\text{-}pz)\}_{31}$ ("Host 12"), which encapsulates the sulfate present in the solution. The structure of Host 9 was determined by electrospray ionization mass spectrometry, which does not differentiate between possible ring sets.

For example, in laboratory scale synthesis of Host 12, 15.007 g of $CuSO_4.5H_2O$ (60.1 mmol), 4.690 g NaOH pellets (117.3 mmol), 4.092 g pyrazole (60.1 mmol), 19.906 g $Pb(NO_3)_2$ (60.1 mmol) and 3.9 g $Bu_4NOH$ (1M in $H_2O$) (3.9 mmol) were added to 350 ml THF, and stirred for 7 days. A white solid ($PbSO_4$, $NaNO_3$) was then removed from the deep blue solution by filtration and the solvent was evaporated in vacuum to yield 10.292 g of a dark blue powder. The product was purified by recrystallization from toluene solution by diffusion of hexane vapors. The identity of the product was confirmed to be $(Bu_4N)_2[SO_4^{2-} \subset \{cis\text{-}Cu^{II}(\mu\text{-}OH)(\mu\text{-}pz)\}_{31}]$ exclusively, by electrospray ionization mass spectrometry in acetonitrile solution (ESI–: m/z 2336).

Another embodiment of anion-encapsulating aggregates is based on the formation of ligand-bound pyrazole nano-jars. Long chain alkyl groups, branched alkyl groups or cyclic alkyl groups can be attached to pyrazole for incorporation into the encapsulating host assemblies for increased solubility in non-polar solvents. Additionally, charged ligands can be attached for to pyrazole for incorporation into encapsulating host assemblies to improve solubility in polar solvents, or to create encapsulating host assemblies with altered recognition, binding, or tethering properties, or both.

In particular, one embodiment includes anion-encapsulating aggregates based on encapsulating host assemblies such as $\{cis\text{-}Cu^{II}(\mu\text{-}OH)(\mu\text{-}4\text{-}Mepz)\}_{27}$ ("Host 13"), $\{cis\text{-}Cu^{II}(\mu\text{-}OH)(\mu\text{-}4\text{-}Mepz)\}_{28}$ ("Host 14"), $\{cis\text{-}Cu^{II}(\mu\text{-}OH)(\mu\text{-}4\text{-}Mepz)\}_{29}$ ("Host 15"), $\{cis\text{-}Cu^{II}(\mu\text{-}OH)(\mu\text{-}4\text{-}Mepz)\}_{30}$ ("Host 16"), $\{cis\text{-}Cu^{II}(\mu\text{-}OH)(\mu\text{-}4\text{-}Mepz)\}_{31}$ ("Host 17"), and $\{cis\text{-}Cu^{II}(\mu\text{-}OH)(\mu\text{-}4\text{-}Mepz)\}_{32}$ ("Host 18"). These alkyl ligand-bound pyrazole anion-encapsulating aggregates include 4-methylpyrazole ("4-Mepz") and are somewhat soluble in pentane, hexane and cyclohexane. Hosts 13, 15, and 17 selectively encapsulate both carbonate and sulfate anions. Hosts 14 and 18 selectively encapsulate sulfate anions. Host 16 selectively encapsulates carbonate anions. These encapsulating host assemblies form anion-encapsulating aggregates which are capable of encapsulating anions present as contaminants in aqueous-hydrocarbon solvent mixtures, including without limitation in-process nuclear waste.

In a laboratory scale synthesis, the ligand-bound pyrazole containing anion-encapsulating aggregates were formed by adding 304 mg $CuSO_4 \cdot 5H_2O$ (1.22 mmol), 94 mg NaOH pellets (2.35 mmol), 100 mg 4-methylpyrazole (1.22 mmol) and 79 mg $Bu_4NOH$ (1M in $H_2O$) (0.079 mmol) to 10 ml THF, and stirring for 13 days. A dark brown-purple solid was removed from the deep blue solution by filtration and the solvent was evaporated to yield 72 mg of a dark blue powder. The identity of the products was confirmed by electrospray ionization mass spectrometry in acetonitrile solution (ESI–: $[CO_3^{2-} \subset \{cis\text{-}Cu^{II}(\mu\text{-}OH)(\mu\text{-}4\text{-}Mepz)\}_{27}]^{2-}$ m/z 2212, $[SO_4^{2-} \subset \{cis\text{-}Cu^{II}(\mu\text{-}OH)(\mu\text{-}4\text{-}Mepz)\}_{27}]^{2-}$ m/z 2230, $[SO_4^{2-} \subset \{cis\text{-}Cu^{II}(\mu\text{-}OH)(\mu\text{-}4\text{-}Mepz)\}_{28}]^{2-}$ m/z 2311, $[CO_3^{2-} \subset \{cis\text{-}Cu^{II}(\mu\text{-}OH)(\mu\text{-}4\text{-}Mepz)\}_{29}]^{2-}$ m/z 2374, $[SO_4^{2-} \subset \{cis\text{-}Cu^{II}(\mu\text{-}OH)(\mu\text{-}4\text{-}Mepz)\}_{29}]^{2-}$ m/z 2392, $[CO_3^{2-} \subset \{cis\text{-}Cu^{II}(\mu\text{-}OH)(\mu\text{-}4\text{-}Mepz)\}_{30}]^{2-}$ m/z 2455, $[CO_3^{2-} \subset \{cis\text{-}Cu^{II}(\mu\text{-}OH)(\mu\text{-}4\text{-}Mepz)\}_{31}]^{2-}$ m/z 2536, $[SO_4^{2-} \subset \{cis\text{-}Cu^{II}(\mu\text{-}OH)(\mu\text{-}4\text{-}Mepz)\}_{31}]^{2-}$ m/z 2554, $[SO_4^{2-} \subset \{cis\text{-}Cu^{II}(\mu\text{-}OH)(\mu\text{-}4\text{-}Mepz)\}_{32}]^{2-}$ m/z 2634).

Another embodiment of an anion-encapsulating host containing a longer chain ligand-bound pyrazole is based on the formation of encapsulating host assemblies including 4-butylpyrazole. Anion-encapsulating aggregates incorporating 4-butylpyrazole are very soluble in pentane, hexane and cyclohexane, and are gradually less soluble in longer hydrocarbons (such as heptane, octane, decalin, and hexadecane). These anion-encapsulating aggregates can be used to encapsulate anions present as contaminants in aqueous-hydrocarbon solvent mixtures, such as those present in in-process nuclear waste.

Further, specific ligand-bound pyrazole-containing anion-encapsulating aggregates can also be formed by combining a particular metal with copper during the formation of the aggregate.

When a particular metal is added to the copper in preparation of the anion-encapsulating aggregate, the result may be a homogenous batch of anion-encapsulating aggregates with a particular copper oxidation state, number of atoms, and targeted encapsulated anion. When a different metal is added to the copper in preparation of the anion-encapsulating aggregate, the result may be a heterogeneous mixture of anion-encapsulating aggregates with a plurality of different copper oxidation states, copper atoms, and targeted encapsulated anions.

For example, where Host 17 is permitted to form anion-encapsulating aggregates in the presence of lead, it encapsulates sulfate ions, to form $(Bu_4N)_2[SO_4^{2-} \subset \{cis\text{-}Cu^{II}(\mu\text{-}OH)(\mu\text{-}4\text{-}Mepz)\}_{31}]$. In a laboratory scale synthesis, 304 mg $CuSO_4 \cdot 5H_2O$ (1.22 mmol), 94 mg NaOH pellets (2.35 mmol), 100 mg 4-methylpyrazole (1.22 mmol), 423 mg $Pb(NO_3)_2$ (1.28 mmol) and 79 mg $Bu_4NOH$ (1M in $H_2O$) (0.079 mmol) were added to 10 ml THF, and stirred for 7 days. A gray-purple solid was removed from the deep blue solution by filtration and the solvent was evaporated to yield 96 mg of a dark blue powder, $(Bu_4N)_2[SO_4^{2-} \subset \{cis\text{-}Cu^{II}(\mu\text{-}OH)(\mu\text{-}4\text{-}Mepz)\}_{31}]$. The identity of the product was confirmed by electrospray ionization mass spectrometry in acetonitrile solution (ESI–: m/z 2554).

When other metals are used in place of lead in the above described reaction, alternative anion-encapsulating aggregates can be formed. For example, when the following metal anions were used with the copper sulfate anion-encapsulating aggregates based on Host 14 which selectively encapsulate sulfates were formed: $Pb^{2+}$, $Ca^{2+}$, $Co^{2+}$, $Mn^{2+}$, $Pr^{3+}$, and $Nd^{3+}$. Alternatively, when $Zn^{2+}$, $Cd^{2+}$, or $Ni^{2+}$ are present during the formation of the anion-encapsulating aggregate, the result is a mixture of sulfate anion-encapsulating aggregates based on Host 13, Host 14, Host 15, and Host 17.

As with 4-methylpyrazole, described above, when 4-butylpyrazole is added to copper in the presence of another metal, the 4-butylpyrazole-based anion-encapsulating aggregates form to selectively encapsulate a desired target anion, to the exclusion of other anions. When the 4-butylpyrazole is added to copper in the presence of another metal, the result may be a homogenous batch of anion-encapsulating aggregates with a particular copper oxidation state, number of atoms, and targeted encapsulated anion. When a different metal is added to the copper in preparation of the ion encapsulating aggregate, the result may be a heterogeneous mixture of anion-encapsulating aggregates with a plurality of different copper oxidation states, copper atoms, and targeted encapsulated anions.

A variety of cation counterions can be used to form the lids for the nano-jars, including smaller alkali or alkaline-earth metal counterions. In one example, 4-butylpyrazole is added to a solution containing copper in the presence of cesium, to form a carbonate encapsulating aggregate. In a laboratory scale synthesis, 187 mg $Cu(NO_3)_2 \cdot 2.5H_2O$ (0.804 mmol), 320 mg $CsOH \cdot H_2O$ (containing ≤10% $Cs_2CO_3$) and 100 mg 4-butylpyrazole (0.805 mmol) were added to 10 ml THF, and stirred for 4 days. A dark brown wet residue was removed from the deep blue solution by filtration and the solvent was evaporated to yield 171 mg of a dark blue powder. The identity of the product as $Cs_2[CO_3^{2-} \subset \{cis\text{-}Cu^{II}(\mu\text{-}OH)(\mu\text{-}4\text{-}Bupz)\}_{27}]$ was confirmed by electrospray ionization mass spectrometry in tetrahydrofuran solution (ESI–: m/z 2780).

The use of alternate counterions, such as rubidium, potassium, and/or sodium, resulted in heterogeneous mixtures containing varying amounts of anion-encapsulating aggregates based on the following encapsulating host assemblies: $\{cis\text{-}Cu^{II}(\mu\text{-}OH)(\mu\text{-}4\text{-}Bupz)\}_{27}$, $\{cis\text{-}Cu^{II}(\mu\text{-}OH)(\mu\text{-}4\text{-}Bupz)\}_{29}$, and $[cis\text{-}Cu^{II}(\mu\text{-}OH)(\mu\text{-}4\text{-}Bupz)\}_{31}$. The anion-encapsulating aggregates had the general formulas of $M_2[CO_3^{2-} \subset \{cis-Cu^{II}(\mu-OH)(\mu-4-Bupz)\}_{27}]$, $M_2[CO_3^{2-} \subset \{cis-Cu^{II}(\mu-OH)(\mu-4-Bupz)\}_{29}]$ and $M_2[CO_3^{2-} \subset \{cis-Cu^{II}(\mu-OH)(\mu-4-Bupz)\}_{31}]$, where $M=Rb^+$, $K^+$ or $Na^+$. The three products were identified by electrospray ionization mass spectrometry in acetonitrile solution (ESI–: m/z 2780, 2984 and 3188).

In one laboratory scale synthesis, 187 mg $Cu(NO_3)_2 \cdot 2.5H_2O$ (0.804 mmol), 235 mg $RbOH \cdot H_2O$ (containing ≤15% $Rb_2CO_3$) and 100 mg 4-butylpyrazole (0.805 mmol) were added to 10 ml THF, and stirred for 7 days. A dark brown wet residue was removed from the deep blue solution by filtration and the solvent was evaporated to yield 137 mg of a dark blue powder, where the dark blue powder is $Rb_2[CO_3^{2-} \subset \{cis-Cu^{II}(\mu-OH)(\mu-4-Bupz)\}_{27}]$, $Rb_2[CO_3^{2-} \subset \{cis-Cu^{II}(\mu-OH)(\mu-4-Bupz)\}_{29}]$ and $Rb_2[CO_3^{2-} \subset \{cis-Cu^{II}(\mu-OH)(\mu-4-Bupz)\}_{31}]$.

In another laboratory scale synthesis, 187 mg $Cu(NO_3)_2 \cdot 2.5H_2O$ (0.804 mmol), 106 mg KOH 85% (1.61 mmol), 100 mg 4-butylpyrazole (0.805 mmol) and 10 mg $K_2CO_3$ (0.0724 mmol) were added to 10 ml THF, and stirred for 3 days. A small amount of brown residue was removed from the deep blue solution by filtration and the solvent was evaporated to yield 172 mg of a dark blue powder, where the dark blue powder is $K_2[CO_3^{2-} \subset \{cis-Cu^{II}(\mu-OH)(\mu-4-Bupz)\}_{27}]$, $K_2[CO_3^{2-} \subset \{cis-Cu^{II}(\mu-OH)(\mu-4-Bupz)\}_{29}]$ and $K_2[CO_3^{2-} \subset \{cis-Cu^{II}(\mu-OH)(\mu-4-Bupz)\}_{31}]$.

In another laboratory scale synthesis, 187 mg $Cu(NO_3)_2 \cdot 2.5H_2O$ (0.804 mmol), 70 mg NaOH (1.75 mmol), 100 mg 4-butylpyrazole (0.805 mmol) and 12 mg $Na_2CO_3H_2O$ (0.0968 mmol) were added to 10 ml THF, and stirred for 4 days. A dark brown residue was removed from the deep blue solution by filtration and the solvent was evaporated to yield 164 mg of a dark blue powder, where the dark blue powder is $Na_2[CO_3^{2-} \subset \{cis-Cu^{II}(\mu-OH)(\mu-4-Bupz)\}_{27}]$, $Na_2[CO_3^{2-} \subset \{cis-Cu^{II}(\mu-OH)(\mu-4-Bupz)\}_{29}]$ and $Na_2[CO_3^{2-} \subset \{cis-Cu^{II}(\mu-OH)(\mu-4-Bupz)\}_{31}]$.

In another laboratory scale synthesis, 201 mg $CuSO_4 \cdot 5H_2O$ (0.80 mmol), 67 mg NaOH (containing ≤5% $Na_2CO_3$), 100 mg 4-butylpyrazole (0.80 mmol) and 30 mg (0.0523 mmol) bis(triphenylphosphoranylidene) ammonium chloride ("PPNCl") were added to 10 ml THF, and stirred for 4 days. A dark brown wet residue was removed from the deep blue solution by filtration and the solvent was evaporated to yield 174 mg of a dark blue residue. The identity of the products was confirmed by electrospray ionization mass spectrometry in acetonitrile solution (ESI–: m/z 2780 and 2900) to be $(PPN)_2[CO_3^{2-} \subset \{cis-Cu^{II}(\mu-OH)(\mu-4-Bupz)\}_{27}]$ and $(PPN)_2[SO_4^{2-} \subset \{cis-Cu^{II}(\mu-OH)(\mu-4-Bupz)\}_{28}]$.

In addition to direct formation of ligand-bound pyrazoles in the formation of a nano-jar, a variety of ligand bound pyrazoles can be substituted for non-ligand bound pyrazoles that have already been incorporated into an anion-encapsulating aggregate. For example, long chain alkyl groups, branched alkyl groups, or cyclic alkyl groups that are attached to a pyrazole can be incorporated into anion host assemblies for increased solubility in non-polar solvents by substitution of the ligand-bound pyrazole for the pyrazole present in the anion host assembly. Additionally, charged ligands bound to pyrazole can be substituted for pyrazole in the anion host assembly, or to improve anion host assembly's solubility in polar solvents, to create anion host assemblies with altered recognition, binding, tethering or other properties (with respect to the original anion host assembly), or both. There are certain ligands which are more easily incorporated into an anion-encapsulating aggregate through substitution than during de novo formation of the anion-encapsulating aggregate. Examples of such ligands include chloride ($Cl^-$), bromide ($Br^-$), and iodide ($I^-$).

In one embodiment, to perform a ligand exchange reaction, or a substitution, with chloropyrazole on a laboratory scale, 100 mg $(Bu_4N)_2[SO_4^{2-} \subset \{cis-Cu^{II}(\mu-OH)(\mu-pz)\}_{31}]$ (0.0194 mmol) and 100 mg 4-chloropyrazole (0.975 mmol) were dissolved into 10 ml THF. A small aliquot was immediately diluted with acetonitrile and subjected to analysis by electrospray ionization mass spectrometry. Two minutes after mixing, a mixture of $[(SO_4^{2-})Cu_{31}(\mu-OH)_{31}(\mu-pz)_x(\mu-4-Clpz)_{31-x}]$ species (x=5-15) was identified, with $[(SO_4^{2-})Cu_{31}(\mu-OH)_{31}(\mu-pz)_{10}(\mu-4-Clpz)_{21}]$ as the most abundant species. Twelve minutes after mixing, x=2-13, and the most abundant species was $[(SO_4^{2-})Cu_{31}(\mu-OH)_{31}(\mu-pz)_8(\mu-4-Clpz)_{23}]$. Forty-two minutes after mixing, x=1-12, and the most abundant species was $[(SO_4^{2-})Cu_{31}(\mu-OH)_{31}(\mu-pz)_6(\mu-4-Clpz)_{25}]$. The same distribution was found seventeen hours after mixing.

In another embodiment, to perform a ligand exchange reaction with bromopyrazole on a laboratory scale, 50 mg $(Bu_4N)_2[SO_4^{2-} \subset \{cis-Cu^{II}(\mu-OH)(\mu-pz)\}_{31}]$ (0.00969 mmol) and 87 mg 4-bromopyrazole (0.592 mmol) were dissolved into 10 ml THF. A small aliquot was immediately diluted with acetonitrile and subjected to analysis by electrospray ionization mass spectrometry. Two minutes after mixing, a mixture of $[(SO_4^{2-})Cu_{31}(\mu-OH)_{31}(\mu-pz)_x(\mu-4-Brpz)_{31-x}]$ species (x=3-12) was identified, the species with x=7 and 8 being the most abundant. Twelve minutes after mixing, x=2-11, and the most abundant species was $[(SO_4^{2-})Cu_{31}(\mu-OH)_{31}(\mu-pz)_7(\mu-4-Brpz)_{24}]$. Forty-two minutes after mixing, x=1-10, and the most abundant species was $[(SO_4^{2-})Cu_{31}(\mu-OH)_{31}(\mu-Pz)_5(\mu-4-Brpz)_{26}]$. The same distribution was found seventeen hours after mixing.

In another embodiment, to perform a ligand exchange reaction with iodopyrazole on a laboratory scale, 50 mg $(Bu_4N)_2[SO_4^{2-} \subset \{cis-Cu^{II}(\mu-OH)(\mu-pz)\}_{31}]$ (0.00969 mmol) and 118 mg 4-iodopyrazole (0.608 mmol) were dissolved into 5 ml THF. A small aliquot was immediately diluted with acetonitrile and subjected to analysis by electrospray ionization mass spectrometry. Two minutes after mixing, a mixture of $[(SO_4^{2-})Cu_{31}(\mu-OH)_{31}(\mu-pz)_x(\mu-4-Ipz)_{31-x}]$ species (x=3-11) was identified, with x=7 being the most abundant species. Twelve minutes after mixing, x=2-10, and the species with x=4 and 5 were the most abundant. Forty-two minutes after mixing, x=1-8, and the most abundant species was with $[(SO_4^{2-})Cu_{31}(\mu-OH)_{31}(\mu-pz)_x(\mu-4-Ipz)_{27}]$.

In another embodiment, ethylene-bridged pyrazole, with 2 pyrazole linked by 2 $CH_2$ groups, can be used in place of pyrazole in anion-encapsulating aggregates. In one method of forming the ethylene-bridged pyrazole (also denoted herein as 1,2-bis(1H-pyrazole-3-yl) ethane) diethyl 2,4,7,9-tetraoxodecanedione ("compound 1") is prepared first. In a laboratory scale synthesis forming compound 1 includes the steps of placing small pieces of sodium metal (11.500 g, 500 mmol) in a 1000 ml three-necked round bottom flask equipped with a stir bar, condenser and addition funnel, and connected to a Schlenk line. After evacuation purging with $N_2$, the flask is placed into an ice bath and anhydrous diethyl ether (500 ml) is added by syringe. A mixture of diethyl oxalate (73.000 g, 500 mmol) and 2,5-hexanedione (28.500 g, 250 mmol) is slowly added under stirring, and the dark brown suspension is further stirred for 2 hours at 0° C. After warming up to room temperature overnight under an $N_2$ atmosphere, the reaction mixture is refluxed for 1 hour. The brown suspension is filtered out, washed with diethyl ether, and dried under high vacuum. The solid is then dissolved in dionized water (2 L) and acidified to a pH of about 3 with a 10% aqueous solution of $H_2SO_4$ (200 mL). A light yellowish-brown precipitate forms, which is filtered out and dried under high vacuum (22.310 g). Recrystallization from hot ethanol affords 14.593 g (19%) of compound 1, as shiny brownish plates. NMR in $CDCl_3$ shows the pure enolic form of compound 1. $^1H$ NMR (400 MHz, $CDCl_3$): 6.43 (s, 2H, COCHCOH), 4.34 (q, 4H, $^3J=7.2$ Hz, $CH_3CH_2$), 2.91 (s, 4H, $COCH_2CH_2CO$), 1.36 (t, 6H, $^3J=7.1$ Hz, $CH_3CH_2$) ppm. $^{13}C$ NMR (101 MHz, $CDCl_3$): 202.5, 163.4, 162.0, 102.5, 62.7, 35.3, 14.1 ppm.

Compound 1 is then converted to 1,2-bis(5-carboethoxy-1H-pyrazole-3-yl)ethane ("compound 2"). Hydrazine hydrate (5.05 g, 4.90 mL, 100 mmol) is slowly added to a hot solution of compound 1 (14.000 g, 44.5 mmol) in 100 mL of ethanol. A crystalline solid forms, which is stirred for 30 minutes, filtered, re-crystallized from hot ethanol, and dried under vacuum, resulting in compound 2 (10.215 g, 75%) as a light brown microcrystalline powder. $^1H$ NMR (400 MHz, DMSO-$d_6$): 6.52 (s, 2H, pz-H), 4.24 (q, 4H, $^3J=7.1$ Hz, $CH_3CH_2$), 2.97 (s, 4H, $CH_2CH_2$), 1.27 (t, 6H, $^3J=7.2$ Hz, $CH_3CH_2$) ppm. Compound 2 is used to form 1,2-bis(5-carboxy-1H-pyrazol-3-yl)ethane ("compound 3"). Compound 2 (10.000 g, 32.6 mmol) is dissolved in a 10% aqueous NaOH solution and is boiled for 30 minutes. After cooling, a 20% aqueous $H_2SO_4$ solution is added gradually under stirring to achieve a pH of about 3, resulting in formation of a brown precipitate. The brown precipitate is filtered out, suspended in 37% HCl (250 mL) and boiled for 30 minutes. Filtration and drying in high vacuum affords 9.708 g of compound 3, as a beige powder. $^1H$ NMR (400 MHz, DMSO-$d_6$): 6.48 (s, 2H, pz-H), 2.95 (s, 4H, $CH_2CH_2$) ppm. $^{13}C$ NMR (101 MHz, DMSO-$d_6$): 163.0, 146.9, 141.1, 106.8, 25.8 ppm.

The ethylene-bridged pyrazole, 1,2-bis(1H-pyrazol-3-yl) ethane, is then synthesized from compound 3. A vial is preheated to 330° C. in a sand bath, and then compound 3 (4.6 g, 18.62 mmol) is added to the vial and covered with a watch glass. As compound 3 starts melting, a white smoke is evolved, which condenses onto the watch glass. After all the material has melted (about 3 minutes), the vial is taken out of the sand bath and left to cool to room temperature. The white solid condensed onto the watch glass (about 50 mg) is pure ethylene-bridged pyrazole. The dark brown molten residue in the vial is extracted with boiling ethanol under stirring. After filtration, the ethanolic extract is heated and stirred for 2 hours with activated carbon, then filtered and evaporated to give a yellowish-brown oil (1.5 g). Upon trituration with diethyl ether, pure ethylene-bridged pyrazole is obtained as a pale yellow powder (900 mg, total yield of about 32%). $^1H$ NMR (400 MHz, DMSO-$d_6$): 7.46 (s, 2H, pz-5-H), 6.48 (d, 2H, $^3J=1.8$ Hz, pz-3-H), 2.88 (s, 4H, $CH_2CH_2$) ppm.

The ethylene-bridged pyrazole (also referred to as "$pzCH_2CH_2pz$" below) can then be used to form another embodiment of an anion-encapsulating aggregate based on $\{Cu^{II}{}_n(OH)_n(pzCH_2CH_2pz)\}_{n/2}$, where n=26, 28, 30 ("Host 19"). The encapsulating host assembly Host 19 includes nanojars of $\{Cu^{II}{}_n(OH)_n(pzCH_2CH_2pz)\}_{n/2}$, where n is 26, 28, 30, which serve to encapsulate carbonate ions, forming the compound $CO_3^{2-} \subset \{Cu^{II}{}_n(OH)_n(pzCH_2CH_2pz)\}_{n/2}$. One example of a suitable counterion for forming the lid over the carbonate encapsulating host assemblies is $Bu_4N^+$, resulting in anion-encapsulating aggregates $(Bu_4N)_2$ $[CO_3^{2-} \subset \{Cu^{II}{}_n(OH)_n(pzCH_2CH_2pz)\}_{n/2}]$ (n=26, 28, 30). To use Host 19 for carbonate ion extraction, a solvent, the stoichiometrically required amounts (based on the amount of carbonate to be extracted) of nano-jar ingredients of a copper salt, a base (or a copper hydroxide in place of the copper salt and base) and ethylene-bridged pyrazole, and a counterion contributor (if the base does not act as a counterion contributor) are combined with an aqueous solution containing the carbonate ions, which may or may not be in the presence of competing ions, to form an organic-aqueous mixture with an overall neutral or basic pH level. The copper contributor, hydroxide contributor, and counterion contributor may be three separate compounds, or one compound may perform as a contributor of more than one of copper, hydroxide and counterions. The components in the organic-aqueous mixture are permitted to react, after which the carbonate is encapsulated in the Host 19 ring assemblies, found in the organic phase of the organic-aqueous mixture. The organic layer of the organic aqueous mixture can then be separated from the aqueous layer using known separation techniques, such as the use of a separatory funnel.

In an alternate embodiment, a polymer chain of $[Cu^{II}{}_n (OH)_n(pzCH_2CH_2pz)]_\infty$ and a counterion contributor can be combined with an aqueous solution containing carbonate ions to form an organic-aqueous mixture with an overall neutral or basic pH level, as described above. The components in the organic-aqueous mixture are permitted to react, after which the carbonate is encapsulated into the Host 19 ring assemblies, which are found in the organic phase of the organic-aqueous mixture. The organic layer of the organic-aqueous mixture can then be separated from the aqueous layer using known separation techniques, such as the use of a separatory funnel.

In one laboratory scale experiment, 143 mg of $Cu(NO_3)_2 \cdot 2.5H_2O$ (0.615 mmol), 48.0 mg of NaOH (1.20 mmol), 50.0 mg of 1,2-bis(1H-pyrazol-3-yl)ethane ($HpzCH_2CH_2pzH$) (0.308 mmol), 76.0 mg of $Na_2CO_3 \cdot H_2O$ (0.613 mmol) and 44 mg of $Bu_4NOH$ (1M in $H_2O$) (0.044 mmol) are added to 10 ml THF, and stirred for 4 days. A dark brown-grey solid is removed from the deep blue solution by filtration and the solvent is evaporated to yield 112 mg dark blue powder. Electrospray ionization mass spectrometry in acetonitrile solution indicates that the product contains $[CO_3 \subset \{Cu^{II}{}_{26}(OH)_{26}(pzCH_2CH_2pz)\}_{13}]^{2-}$ (ESI-: m/z 4237), $[CO_3 \subset \{Cu^{II}{}_{28}(OH)_{28}(pzCH_2CH_2pz)\}_{14}]^{2-}$ (ESI-: m/z 4558) and $[CO_3 \subset \{Cu^{II}{}_{30}(OH)_{30}(pzCH_2CH_2pz)\}_{15}]^{2-}$ (ESI-: m/z 4880).

The same experiment was repeated with $CuSO_4 \cdot 5H_2O$ (154 mg, 0.617 mmol) instead of $Cu(NO_3)_2 \cdot 2.5H_2O$ and without $Na_2CO_3 \cdot H_2O$. In contrast to the previous experiment, there was no apparent reaction after 4 days. After three weeks, however, as $CO_2$ from air was gradually absorbed by the reaction mixture, a blue solution formed. Electrospray ionization mass spectrometry indicates that the same carbonate-encapsulating nanojar mixture formed as before, when carbonate was deliberately added from the beginning, and no sulfate-encapsulating nanojars could be detected. Therefore, these experiments demonstrate that the nano-jars formed by ethylene-bridged pyrazole are totally selective for carbonate ions over nitrate ions and are largely selective for carbonate ions over sulfate ions, where nano-jars based on simple pyrazole are selective for carbonate over nitrate, but not over sulfate.

In another embodiment, hexylene-bridged pyrazole, with 2 pyrazole linked by 6 $CH_2$ groups (also denoted herein as 1,6-bis(pyrazole-3(5)-yl)hexane), can be used in addition to pyrazole in anion-encapsulating aggregates. In one method of forming the hexylene-bridged pyrazole, 1-(tetrahydropyran-2-yl)pyrazole (5.000 g, 32.85 mmole) is dissolved in anhydrous THF (50 mL) in a Schlenk flask under a dry $N_2$ atmosphere. The solution is chilled to −78° C. by stirring for 15 minutes in a dry-ice/isopropanol bath. $^n$BuLi (1.6 M in hexane, 21 mL, 32.85 mmole) is added dropwise from an $N_2$-purged syringe over 20 minutes. Stirring at −78° C. is continued for another 30 minutes, then 1,6-diiodohexane (10.95 mmol) is added dropwise over 20 minutes. After stirring at −78° C. for 3 hours, the solution is left to warm up overnight (stirred under $N_2$), and then quenched with water (1 mL). The volatiles are removed on a Rotavap, 80 ml water is added to the residue and it is extracted with ethyl acetate (3×80 mL), followed by washing with brine (80 mL) and drying with anhydrous $MgSO_4$. After removing the volatiles on the Rotavap, the residue is washed with hexane to remove the unreacted 1-(tetrahydropyran-2-yl)pyrazole. Pure 1,6-bis(1-(tetrahydropyran-2-yl)pyrazol-5-yl)hexane is obtained in 80% yield. $^1$H NMR (400 MHz, $CDCl_3$): 7.45 (d, 2H, $^3$J=1.4 Hz, 3-H-pz), 6.03 (d, 2H, $^3$J=1.4 Hz, 4-H-pz), 5.23 (dd, 2H, $^3$J=9.9 Hz, $^3$J=2.6 Hz, CH-THP), 3.99-4.05 (m, 2H, $CH_2$O-THP), 3.58-3.66 (m, 2H, $CH_2$O-THP), 2.59-2.73 (m, 4H, $CH_2(CH_2)_4$—$CH_2$), 2.44-2.55 (m, 2H, $CH_2$-THP), 2.06-2.14 (m, 2H, $CH_2$-THP), 1.90-1.97 (m, 2H, $CH_2$-THP), 1.54-1.77 (m, 10H, $CH_2$-THP and $CH_2CH_2(CH_2)_2CH_2CH_2$), 1.38-1.47 (m, 4H, $(CH_2)_2(CH_2)_2(CH_2)_2$) ppm. $^{13}$C NMR (101 MHz, $CDCl_3$): 143.8, 139.1, 105.0/104.9, 84.3/84.1, 67.94/67.85/67.80/67.72, 29.6/29.5, 29.1, 28.5, 25.2, 23.0 ppm.

The free hexylene-bridged pyrazole is prepared by dissolving 1,6-bis(1-(tetrahydropyran-2-yl)pyrazol-5-yl)hexane (20 mmol) in ethanol (200 mL) and adding conc. HCl (10 mL) dropwise under stirring. After stirring overnight at room temperature, the volatiles are removed on a Rotavap at 35° C. and the residual aqueous solution is neutralized with $NaHCO_3$ to pH ∼8. The white precipitate obtained is filtered, washed with water and dried in vacuum at 100° C. Pure 1,6-bis(pyrazol-3(5)-yl)hexane is obtained in 77% yield. $^1$H NMR (400 MHz, DMSO-$d_6$): 7.46 (s, 2H, 3-H-pz), 6.02 (s, 2H, 4-H-pz), 2.55 (t, 4H, $^3$J=7.7 Hz, $CH_2(CH_2)_4CH_2$), 1.56 (m, 4H, $CH_2CH_2(CH_2)_2CH_2CH_2$), 1.30 (m, 4H, $(CH_2)_2(CH_2)_2(CH_2)_2$) ppm. $^{13}$C NMR (101 MHz, DMSO-$d_6$): 147.2, 134.8, 103.4, 29.5, 29.0, 26.5 ppm.

The hexylene-bridged pyrazole can then be used to form another embodiment of an anion-encapsulating aggregate based on $\{Cu^{II}_n(OH)_n(pz)_{n-2x}(pz(CH_2)_6pz)\}_x$, where n is 27, 28, 29, 30, 31 ("Host 20"). The encapsulating host assembly Host 20 includes nano-jars of $\{Cu^{II}_n(OH)_n(pz)_{n-2x}(pz(CH_2)_6pz)\}_x$, where n is 27, 28, 29, 30, 31, which serve to encapsulate carbonate ions, forming the compound $CO_3^{2-} \subset \{Cu^{II}_n(OH)_n(pz)_{n-2x}(pz(CH_2)_6pz)\}_x$, where n is 27, 28, 29, 30, 31. One example of a suitable counterion for forming the lid over the carbonate encapsulating host assemblies is $Bu_4N^+$, resulting in anion-encapsulating aggregates $(Bu_4N)_2[CO_3^{2-} \subset \{Cu^{II}_n(OH)_n(pz)_{n-2x}(pz(CH_2)_6pz)\}_x]$, where n is 27, 28, 29, 30, 31. In use, nano-jars including Host 20 are preferably combined with nano-jars including unbridged pyrazole to effectively encapsulate the target anions. To use Host 20 for carbonate ion extraction, a solvent, the stoichiometrically required amounts (based on the amount of carbonate to be extracted) of nano-jar ingredients of a copper salt a base (or a copper hydroxide in place of the copper salt and base), hexylene-bridged pyrazole, pyrazole, and a counterion contributor (if the base does not act as a counterion contributor) are combined with an aqueous solution containing the carbonate ions, which may or may not be in the presence of competing ions, to form an organic-aqueous mixture that has an overall neutral or basic pH level. The copper contributor, hydroxide contributor, and counterion contributor may be three separate compounds, or one compound may perform as a contributor of more than one of copper, hydroxide and counterions. The components in the organic-aqueous mixture are permitted to react, after which the carbonate is encapsulated in the Host 20 ring assemblies and pyrazole ring assemblies, found in the organic phase of the organic-aqueous mixture. The organic layer of the organic aqueous mixture can then be separated from the aqueous layer using known separation techniques, such as the use of a separatory funnel.

In one laboratory scale experiment, 426 mg of $Cu(NO_3)_2.2.5H_2O$ (1.83 mmol), 142 mg of NaOH (3.55 mmol), 100 mg of 1,6-bis(1H-pyrazol-3-yl)hexane (Hpz$(CH_2)_6$pzH) (0.458 mmol), 62.4 mg of pyrazole (0.917 mmol), 228 mg of $Na_2CO_3.H_2O$ (1.84 mmol) and 131 mg of $Bu_4$NOH (1M in $H_2O$) (0.131 mmol) are added to 20 ml THF, and stirred for 9 days. A dark brown solid is removed from the deep blue solution by filtration and the solvent is evaporated to yield a dark blue powder. Electrospray ionization mass spectrometry in acetonitrile solution indicates that the product contains the following ions: $[CO_3 \subset \{Cu^{II}_{27}(OH)_{27}(pz)_{27-2x}(pz(CH_2)_6pz)_x\}]^{2-}$ (x=1-6; ESI-: m/z 2064, 2105, 2146, 2187, 2228, 2269), $[CO_3 \subset \{Cu^{II}_{28}(OH)_{28}(pz)_{28-2x}(pz(CH_2)_6pz)_x\}]^{2-}$ (x=4-6; ESI-: m/z 2261, 2302, 2343), $[CO_3 \subset \{Cu^{II}_{29}(OH)_{29}(pz)_{29-2x}(pz(CH_2)_6pz)_x\}]^{2-}$ (x=1-6; ESI-: m/z 2212, 2253, 2294, 2335, 2376, 2417), $[CO_3 \subset \{Cu^{II}_{30}(OH)_{30}(pz)_{30-2x}(pz(CH_2)_6pz)_x\}]^{2-}$ (x=4-7; ESI-: m/z 2409, 2450, 2491, 2532), $[CO_3 \subset \{Cu^{II}_{31}(OH)_{31}(pz)_{31-2x}(pz(CH_2)_6pz)_x\}]^{2-}$ (x=1-5; ESI-: m/z 2359, 2400, 2441, 2482, 2524).

Another embodiment of an anion-encapsulating aggregate is based on the compounds $\{cis-Cu^{II}(\mu-OH)(\mu-4-F_3Cpz)\}_{27}$ host assembly ("Host 21"), $\{cis-Cu^{II}(\mu-OH)(\mu-4-F_3Cpz)\}_{29}$ host assembly ("Host 22") and $\{cis-Cu^{II}(\mu-OH)(\mu-4-F_3Cpz)\}_{31}$ host assembly ("Host 23"), where 4-$F_3$Cpz is the charged, ligand-bound pyrazole, 4-trifluoromethylpyrazole. Host 21, Host 22, and Host 23 selectively encapsulate carbonate ions. In a laboratory scale synthesis, Host 21, Host 22, and Host 23 were formed by adding 85.5 mg $Cu(NO_3)_2.2.5H_2O$ (0.368 mmol), 28.4 mg NaOH (0.710 mmol), 50.0 mg 4-trifluoromethylpyrazole (0.367 mmol), 24.5 mg $Bu_4$NOH (1M in $H_2O$) (0.0245 mmol) and 45.6 mg $Na_2CO_3.H_2O$ (0.368 mmol) to 10 mL THF, and stirring for 3 days. A light brown solid was removed from the deep blue solution by filtration and the solvent was evaporated to yield 92 mg of a dark blue powder. The identity of the products was confirmed by electrospray ionization mass spectrometry in acetonitrile solution (ESI-: $[CO_3^{2-} \subset \{cis-Cu^{II}(\mu-OH)(\mu-4-F_3Cpz)\}_{27}]^{2-}$ m/z 2941, $[CO_3^{2-} \subset \{cis-Cu^{II}(\mu-OH)(\mu-4-F_3Cpz)\}_{29}]^{2-}$ m/z 3156, $[CO_3^{2-} \subset \{cis-Cu^{II}(\mu-OH)(\mu-4-F_3Cpz)\}_{31}]^{2-}$ m/z 3372. In addition to the nano-jars, a hexanuclear species $[Cu_6^{II}(\mu_3-O)_2(\mu-4-F_3Cpz)_9]^-$ (m/z 1629) was also observed.

Another preferred embodiment of an anion-encapsulating aggregate is based on the encapsulating host assembly including a dimethylpyrazolate anion (a pyrazole with two methyl groups attached thereto), $\{cis-Cu^{II}_n(\mu-OH)_n(\mu-pz)_x(\mu-Me_2pz)_{n-x}\}$, where n is 27, 28, 29, 30, 31. The encapsulating host assemblies show selectivity for the encapsulation of carbonate and sulfate anions, to form $SO_4^{2-} \subset \{cis-Cu^{II}_n(\mu-OH)_n(\mu-pz)_x(\mu-Me_2pz)_{n-x}\}$ and $CO_3^{2-} \subset \{cis-Cu^{II}_n(\mu-OH)_n(\mu-pz)_x(\mu-Me_2pz)_{n-x}\}$. In a laboratory example, the encapsulating host assembly is prepared from a copper(II) ion source, a base, a counterion, and a mixture of pyrazole and 3,5-dimethylpyrazole (using 5:0, 5:1, 5:5, 1:5, and 0:5 molar ratios) in the presence of sulfate and/or carbonate ions. The selectivity can be monitored by electrospray ionization mass spectrometry. No selectivity for sulfate over carbonate was observed with the 5:0, 5:1, 5:5, and 1:5 molar ratios, which yielded nano-jars with both sulfate and carbonate encapsulated as $[CO_3^{2-}$ or $SO_4^{2-} \subset \{cis\text{-}Cu^{II}_{27}(\mu\text{-}OH)_{27}(\mu\text{-}pz)_x(\mu\text{-}Me_2pz)_{27-x}\}]$, $[CO_3^{2-}$ or $SO_4^{2-} \subset \{cis\text{-}Cu^{II}_{28}(\mu\text{-}OH)_{28}(\mu\text{-}pz)_x(\mu\text{-}Me_2pz)_{28-x}\}]$, $[CO_3^{2-}$ or $SO_4^{2-} \subset \{cis\text{-}Cu^{II}_{29}(\mu\text{-}OH)_{29}(\mu\text{-}pz)_x(\mu\text{-}Me_2pz)_{29-x}\}]$, and $[CO_3^{2-}$ or $SO_4^{2-} \subset \{cis\text{-}Cu^{II}_{30}(\mu\text{-}OH)_{30}(\mu\text{-}pz)_x(\mu\text{-}Me_2pz)_{30-x}\}]$. No nano-jars formed when a 0:5 ratio of the two ligands was used. The failure to form nano-jars at this ratio is possibly due to steric hindrance created by the methy substituents in the 3- and 5-positions of the pyrazole ligand. To enhance solubility in extraction solvents used on industrial scale (such as long saturated hydrocarbons), of the nanojars formed with the two pyrazole ligands, the 4-position of the two ligands can be functionalized with n-octyl groups, which impart solubility to the nanojars in saturated hydrocarbons as long as $C_{16}$ (hexadecane).

In another set of embodiments, indazole can be used in place of pyrazole in the anion-encapsulating aggregates, to encapsulate various anions. To form anion-encapsulating aggregates using indazole, the solvent can be combined with the nano-jar components, including a copper salt, indazole as the encapsulating anion, and a base with an aqueous solution containing the anion(s) to be extracted to form an organic-aqueous mixture that has an overall neutral or basic pH level, as described above. Similarly, to form the anion-encapsulating aggregates including indazole, a solvent, a polymer chain of $[Cu^{II}(\mu\text{-}OH)(\mu\text{-}ind)]_\infty$, and an optional counter ion contributor can be added to an aqueous solution containing the targeted anion for extraction to form the organic-aqueous mixture that has an overall neutral or basic pH level. In either case, the components of the organic-aqueous mixture are permitted to react, allowing nano-jars to assemble around the targeted anions and transfer into the organic phase, selectively removing the target anion from the aqueous phase. Separation of the organic phase from the aqueous phase results in extraction of some or all of the targeted anions from the aqueous phase.

One preferred embodiment of an anion-encapsulating aggregate is based on the encapsulating host assembly $\{cis\text{-}Cu^{II}(\mu\text{-}OH)(\mu\text{-}ind)\}_n$, where n is 28, 29, or 31, and ind is indazolate. The encapsulating host assemblies show selectivity for the encapsulation of sulfate ions, as shown in the following laboratory example. 634 mg of $CuSO_4.5H_2O$ (2.54 mmol), 197 mg of NaOH pellets (4.92 mmol), 300 mg of indazole (2.54 mmol) and 200 mg of $Bu_4NOH$ (1M in $H_2O$) (0.200 mmol) were added to 20 ml THF, and stirred for 3 days. A dark brown solid (403 mg) was removed from the deep blue-green solution by filtration and the solvent was evaporated to yield 543 mg dark blue-green powder. Electrospray ionization mass spectrometry in acetonitrile solution indicates that the product is a mixture of $(Bu_4N)_2[SO_4^{2-} \subset \{cis\text{-}Cu^{II}(\mu\text{-}OH)(\mu\text{-}ind)\}_{29}]$ (ESI–: m/z 2914) and $(Bu_4N)_2[SO_4^{2-} \subset \{cis\text{-}Cu^{II}(\mu\text{-}OH)(\mu\text{-}ind)\}_{31}]$ (ESI–: m/z 3112).

A pure version of $\{cis\text{-}Cu^{II}(\mu\text{-}OH)(\mu\text{-}ind)\}_{31}$ can be formed by adding 634 mg of $CuSO_4.5H_2O$ (2.54 mmol), 197 mg of NaOH pellets (4.92 mmol), 300 mg of indazole (2.54 mmol), 920 mg of $Pb(NO_3)_2$ (2.78 mmol) and 164 mg of $Bu_4NOH$ (1M in $H_2O$) (0.164 mmol) to 20 ml THF, and stirring for 7 days. A light grey solid (1.280 g) is removed from the deep blue-green solution by filtration and the solvent is evaporated to yield 596 mg of a dark blue-green powder. Electrospray ionization mass spectrometry in acetonitrile solution indicates that the product consists of $(Bu_4N)_2[SO_4^{2-} \subset \{cis\text{-}Cu^{II}(\mu\text{-}OH)(\mu\text{-}ind)\}_{31}]$ (ESI–: m/z 3112).

Another preferred embodiment of an anion-encapsulating aggregate is based on the encapsulating host assembly $\{cis\text{-}Cu^{II}(\mu\text{-}OH)(\mu\text{-}ind)\}_n$, where n is 29 or 31. The encapsulating host assemblies show selectivity for the encapsulation of selenite, to form $SeO_4^{2-} \subset \{cis\text{-}Cu^{II}(\mu\text{-}OH)(\mu\text{-}ind)\}_n$, where n is 29, 31, as shown in the following laboratory example. 753 mg of $CuSeO_4.5H_2O$ (2.54 mmol), 197 mg of NaOH pellets (4.92 mmol), 300 mg of indazole (2.54 mmol) and 164 mg of $Bu_4NOH$ (1M in $H_2O$) (0.164 mmol) are added to 20 ml THF, and stirred for 4 days. A dark brown residue (491 mg) is removed from the deep blue-green solution by filtration and the solvent is evaporated to yield 549 mg dark blue-green powder. Electrospray ionization mass spectrometry in acetonitrile solution shows the presence of $(Bu_4N)_2[SeO_4^{2-} \subset \{cis\text{-}Cu^{II}(\mu\text{-}OH)(\mu\text{-}ind)\}_{29}]$ (ESI–: m/z 2938) and $(Bu_4N)_2[SeO_4^{2-} \subset \{cis\text{-}Cu^{II}(\mu\text{-}OH)(\mu\text{-}ind)\}_{31}]$ (ESI–: m/z 3136).

Another preferred embodiment of an anion-encapsulating aggregate is based on the encapsulating host assembly $\{cis\text{-}Cu^{II}(\mu\text{-}OH)(\mu\text{-}ind)\}_n$, where n is 28, 29, 30, 31. The encapsulating host assemblies show selectivity for the encapsulation of selenite to form $SeO_3^{2-} \subset \{cis\text{-}Cu^{II}(\mu\text{-}OH)(\mu\text{-}ind)\}_n$, where n is 28, 29, 30, 31, as shown in the following laboratory example. 575 mg of $CuSeO_3.2H_2O$ (2.54 mmol), 197 mg of NaOH pellets (4.92 mmol), 300 mg of indazole (2.54 mmol) and 164 mg of $Bu_4NOH$ (1M in $H_2O$) (0.164 mmol) are added to 20 ml THF, and stirred for 4 days. A dark brown residue (543 mg) is removed from the deep blue-green solution by filtration and the solvent is evaporated to yield 483 mg dark blue-green powder. Electrospray ionization mass spectrometry in acetonitrile solution shows the presence of $[SeO_3 \subset \{cis\text{-}Cu^{II}(\mu\text{-}OH)(\mu\text{-}ind)\}_{28}]^{2-}$ (ESI–: m/z 2831), $[SeO_3 \subset \{cis\text{-}Cu^{II}(\mu\text{-}OH)(\mu\text{-}ind)\}_{29}]^{2-}$ (ESI–: m/z 2930), $[SeO_3 \subset \{cis\text{-}Cu^{II}(\mu\text{-}OH)(\mu\text{-}ind)\}_{30}]^{2-}$ (ESI–: m/z 3029) and $[SeO_3 \subset \{cis\text{-}Cu^{II}(\mu\text{-}OH)(\mu\text{-}ind)\}_{31}]^{2-}$ (ESI–: m/z 3128).

Another preferred embodiment of an anion-encapsulating aggregate is based on the encapsulating host assembly $\{cis\text{-}Cu^{II}(\mu\text{-}OH)(\mu\text{-}ind)\}_n$, where n is 27, 28, 29, 30, or 31. These encapsulating host assemblies show selectivity for the encapsulation of carbonate anions, as shown in the following laboratory example. 281 mg of $CuCO_3.Cu(OH)_2$ (1.27 mmol), 95 mg of NaOH pellets (2.38 mmol), 300 mg of indazole (2.54 mmol) and 180 mg of $Bu_4NOH$ (1M in $H_2O$) (0.180 mmol) are added to 20 ml THF, and stirred for 5 days. A brown solid (301 mg) is removed from the deep blue-green solution by filtration and the solvent is evaporated to yield 498 mg dark blue-green powder. Electrospray ionization mass spectrometry in acetonitrile solution indicates that the product is a mixture of $(Bu_4N)_2[CO_3^{2-} \subset \{cis\text{-}Cu^{II}(\mu\text{-}OH)(\mu\text{-}ind)\}_{27}]$ (ESI–: m/z 2699), $(Bu_4N)_2[CO_3^{2-} \subset \{cis\text{-}Cu^{II}(\mu\text{-}OH)(\mu\text{-}ind)\}_{28}]$ (ESI–: m/z 2798), $(Bu_4N)_2[CO_3^{2-} \subset \{cis\text{-}Cu^{II}(\mu\text{-}OH)(\mu\text{-}ind)\}_{29}]$ (ESI–: m/z 2896), $(Bu_4N)_2[CO_3^{2-} \subset \{cis\text{-}Cu^{II}(\mu\text{-}OH)(\mu\text{-}ind)\}_{30}]$ (ESI–: m/z 2995), and $(Bu_4N)_2[CO_3^{2-} \subset \{cis\text{-}Cu^{II}(\mu\text{-}OH)(\mu\text{-}ind)\}_{31}]$ (ESI–: m/z 3094).

Another preferred embodiment of an anion-encapsulating aggregate is based on the encapsulating host assembly $\{cis\text{-}Cu^{II}(\mu\text{-}OH)(\mu\text{-}ind)\}_n$, where n is 29, 31. These encapsulating host assemblies show selectivity for the encapsulation of chromate anions, as shown in the following laboratory example. 456 mg of $CuCrO_4$ (2.54 mmol), 197 mg of NaOH pellets (4.92 mmol), 300 mg of indazole (2.54 mmol) and 164 mg of $Bu_4NOH$ (1M in $H_2O$) (0.164 mmol) are added to 20 ml THF, and stirred for 4 days. A brown residue (407 mg) is removed from the dark green solution by filtration and the solvent is evaporated to yield 460 mg dark green powder. Electrospray ionization mass spectrometry in acetonitrile solution shows the presence of $[CrO_4 \subset \{cis\text{-}$ $Cu^{II}(\mu\text{-}OH)(\mu\text{-}ind)\}_{27}]$ (ESI−: m/z 2727) and $[CrO_4 \subset \{cis\text{-}Cu^{II}(\mu\text{-}OH)(\mu\text{-}ind)\}_{28}]$ (ESI−: m/z 2826).

Similarly, the other target anions described herein, including selenate, selenite, sulfite, pyrophosphate, and arsenite, have large hydration energies and will permit formation of anion-encapsulating host assemblies based on a series of compounds of the formula $cis\text{-}Cu^{II}_x(OR)_y(ea)_z$, as described herein, or based on a series of cyclic polymerization isomers of the formula $[cis\text{-}Cu^{II}(\mu\text{-}OH)(\mu\text{-}pz)]$, as described herein.

Generally, as described above, the selective extraction of sulfate, phosphate, arsenate, carbonate, selenate, selenite, sulfite, chromate, tetrafluoroberyllate, phosphate, pyrophosphate and arsenite ions from an aqueous solution can be achieved through the addition of anion-encapsulating host assemblies based on a series of compounds of the formula $cis\text{-}Cu^{II}_x(OR)_y(ea)_z$, where R is H, $CH_3$, or another alkyl group, ea is an encapsulating anion, and each of x, y, and z is equal to an integer between about 1 and 40, inclusive, or a series of cyclic polymerization isomers of the formula $[cis\text{-}Cu^{II}(\mu\text{-}OH)(\mu\text{-}ea)]_n$, where n is an integer between 6 and 16, inclusive. The encapsulating anion has a core with two donor atoms on one side at about 1.3-2.5 angstroms apart, with no other atoms substantially hindering the coordination of these two donor atoms to the copper centers, and with the core of the ligand preferably being no wider than about 6 angstroms. To perform the extraction of these anions from an aqueous solution, a solvent, the components of the encapsulation host assembly (a copper salt, a base, (or copper hydroxide in place of the copper salt and the base) and encapsulating anion, and an optional, suitable counterion contributor (if the base does not act as such), are combined with the aqueous solution containing the target ion to form in an organic-aqueous mixture that has an overall neutral or basic pH level. The components of the organic-aqueous mixture are permitted to react, and upon such reaction, the anion-encapsulating host assemblies begin forming nano-jars around the target anions in-situ in the organic-aqueous mixture. As the nano-jars completely form, they transfer to the organic phase. The organic and aqueous phases can then be separated via traditional separation methods such as a separatory funnel.

Alternatively, rather than adding the individual components of the anion-extracting compound, a solvent, a polymer chain of $[Cu^{II}(\mu\text{-}OH)(\mu\text{-}ea)]_\infty$ and an optional, suitable counterion contributor can be combined with the aqueous solution containing the target anion to form an organic-aqueous mixture that has an overall neutral or basic pH level. The components of the organic-aqueous mixture are permitted to react, and upon such reaction, the anion-encapsulating host assemblies begin forming nano-jars around the target anions in-situ in the organic-aqueous mixture. As the nano-jars completely form, they transfer to the organic phase. The organic and aqueous phases can then be separated via traditional separation methods such as a separatory funnel.

The above description is considered that of the preferred embodiments only. Modifications of the inventions will occur to those skilled in the art and to those who make or use the invention. The various devices and methods of providing user information described herein may also be used in combination or separately. Therefore it is understood that the embodiments shown in the drawings and described above are merely for illustrative purposes and not intended to limit the scope of the invention.

The invention claimed is:

1. An anion-encapsulating compound, comprising:
   an encapsulating host of the formula $cis\text{-}Cu^{II}_x(OR_1)_y(R_2ea)_z$, where $R_1$ is H, $CH_3$, $C_2H_5$, $C_3H_7$, $C_4H_9$ or another alkyl group, $R_2$ is $CH_3$, $C_2H_5$, $C_3H_7$, $C_4H_9$ or another alkyl or charged group, ea is one or more encapsulating anions having a core with two donor atoms on one side at 1.3 angstroms to 2.5 angstroms apart, with no other atoms substantially hindering the coordination of the donor atoms to the copper metal centers, and each of x, y, and z is equal to an integer between about 1 and 40, inclusive.

2. The anion encapsulating compound of claim 1, wherein the encapsulating anions are selected from the group consisting of a methyl pyrazolate anion, a ligand-bound pyrazolate anion, an ethylene-bridged pyrazolate, and an indazolate anion.

3. The anion encapsulating compound of claim 1, wherein the encapsulating anions are a mixture of at least two or more different encapsulating anions wherein the encapsulating anions are selected from the group consisting of a pyrazolate anion, a methyl pyrazolate anion, a ligand-bound pyrazolate anion, an ethylene-bridged pyrazolate, an indazolate anion, and a combination thereof.

4. The anion encapsulating compound of claim 1, wherein the encapsulating anions impart steric hindrance to the coordination of the donor atoms to the copper metal centers.

5. The anion encapsulating compound of claim 4, wherein the encapsulating anions comprise methyl pyrazolate anions, ligand-bound pyrazolate anions, ethylene-bridged pyrazolate anions, indazolate anions, dimethylpyrazolate anions, hexylene-bridged pyrazolate anions, carboxylate anions, formate anions, acetate anions, and combinations therein.

6. The anion-encapsulating compound of claim 1, wherein the encapsulating compound further comprises:
   a counterion lid which associates with the encapsulating host to increase the solubility of the anion-encapsulating compound, wherein the counterion lid is a large cation, an alkali or an alkaline-earth metal.

7. The anion encapsulating compound of claim 6, wherein the counterion lid is chosen from the group consisting of tetrabutylammonium ($Bu_4N^+$), tributylammonium ($Bu_3NH^+$), tetraethylammonium ($Et_4N^+$), triethylammonium ($Et_3NH^+$), 18-crown-6 potassium complex ($K^+$-18C6), tris(1,10-phenanthroline)copper(II) - $[Cu(phen)_3]^{2+}$, bis(triphenylphosphoranylidene)ammonium ($Ph_3P=N=PPh_3^+$), sodium ion, potassium ion, rubidium ion, cesium ion, thallium ion, strontium ion, and barium ion.

8. The anion encapsulating compound of claim 1, wherein the anion-encapsulating compound selectively encapsulates an anion chosen from the group consisting of sulfate, phosphate, arsenate, carbonate, chromate, selenite, selenite, tetrafluoroberyllate, sulfite, pyrophosphate, and arsenite ions.

* * * * *